US011439305B2

(12) United States Patent
Gedamu

(10) Patent No.: US 11,439,305 B2
(45) Date of Patent: Sep. 13, 2022

(54) SYSTEM, METHOD AND KIT FOR 3D BODY IMAGING

(71) Applicant: H3ALTH TECHNOLOGIES INC., Calgary (CA)

(72) Inventor: Elias Gedamu, Calgary (CA)

(73) Assignee: H3ALTH TECHNOLOGIES INC., Calgary (CA)

(*) Notice: Subject to any disclaimer, the term of this patent is extended or adjusted under 35 U.S.C. 154(b) by 291 days.

(21) Appl. No.: 16/624,902

(22) PCT Filed: Jun. 21, 2018

(86) PCT No.: PCT/CA2018/050754
§ 371 (c)(1),
(2) Date: Dec. 19, 2019

(87) PCT Pub. No.: WO2018/232511
PCT Pub. Date: Dec. 27, 2018

(65) Prior Publication Data
US 2020/0129066 A1    Apr. 30, 2020

Related U.S. Application Data

(60) Provisional application No. 62/522,891, filed on Jun. 21, 2017.

(51) Int. Cl.
*A61B 5/00* (2006.01)
*A61B 5/107* (2006.01)
*G06T 17/00* (2006.01)

(52) U.S. Cl.
CPC .......... *A61B 5/0064* (2013.01); *A61B 5/1072* (2013.01); *G06T 17/00* (2013.01);
(Continued)

(58) Field of Classification Search
CPC ..... A61B 5/002; A61B 5/0022; A61B 5/0064; A61B 5/0077; A61B 5/015; A61B 5/1072;
(Continued)

(56) References Cited

U.S. PATENT DOCUMENTS

2001/0030754 A1* 10/2001 Spina ................. G06K 9/00369
356/601
2007/0167837 A1* 7/2007 Moyer .................. A61B 5/103
600/476

(Continued)

FOREIGN PATENT DOCUMENTS

CN    103263249 A  *  8/2013
CN    107126213 A     9/2017
(Continued)

*Primary Examiner* — Katrina R Fujita
(74) *Attorney, Agent, or Firm* — Bryce W. Burnham; Booth Udall Fuller, PLC

(57) ABSTRACT

A system and kit for capturing a 3D image of a body a user includes a plurality of pillar segments being configurable between an assembled configuration and a disassembled configuration. In the assembled configuration, the pillar segments are joined to form one or more upstanding sensing pillars. A plurality of sensors operable to capture image data are distributed along the one or more sensing pillars. The plurality of sensors have fields of view that are overlapping when supported on the sensing pillars. In the disassembled configuration, transportation of the pillar segments is facilitated. The system and kit may be suitable for use at a remote location. Additional functionalities may include a power storage unit, solar charging panels, climate control subsystem, and wireless communication submodule. In operation, the sensing pillars may be enclosed within an enclosure.

20 Claims, 16 Drawing Sheets

(52) U.S. Cl.
CPC ............ *A61B 5/0022* (2013.01); *A61B 5/0077* (2013.01); *G06T 2207/30196* (2013.01)

(58) Field of Classification Search
CPC .......... A61B 5/1079; A61B 2560/0247; G06T 17/00; G06T 2207/30196
See application file for complete search history.

(56) References Cited

U.S. PATENT DOCUMENTS

| | | | |
|---|---|---|---|
| 2010/0277571 | A1 | 11/2010 | Xu et al. |
| 2013/0179288 | A1* | 7/2013 | Moses ................ G06K 9/00369 |
| | | | 705/26.1 |
| 2013/0222684 | A1 | 8/2013 | Mueller et al. |
| 2013/0315475 | A1* | 11/2013 | Song ....................... G06T 7/593 |
| | | | 382/154 |
| 2014/0340479 | A1 | 11/2014 | Moore et al. |
| 2015/0037771 | A1* | 2/2015 | Kaleal, III ............. A61B 5/486 |
| | | | 434/257 |
| 2016/0247017 | A1* | 8/2016 | Sareen ..................... G06T 19/00 |
| 2016/0302722 | A1* | 10/2016 | Ashkanani ............. A61B 5/015 |
| 2017/0150064 | A1* | 5/2017 | Mayer ........................ G06T 7/11 |
| 2018/0184977 | A1* | 7/2018 | Nahmias ............... A61B 5/0077 |

FOREIGN PATENT DOCUMENTS

| | | |
|---|---|---|
| KR | 101777229 B1 | 9/2017 |
| WO | 2018011330 A1 | 1/2018 |

\* cited by examiner

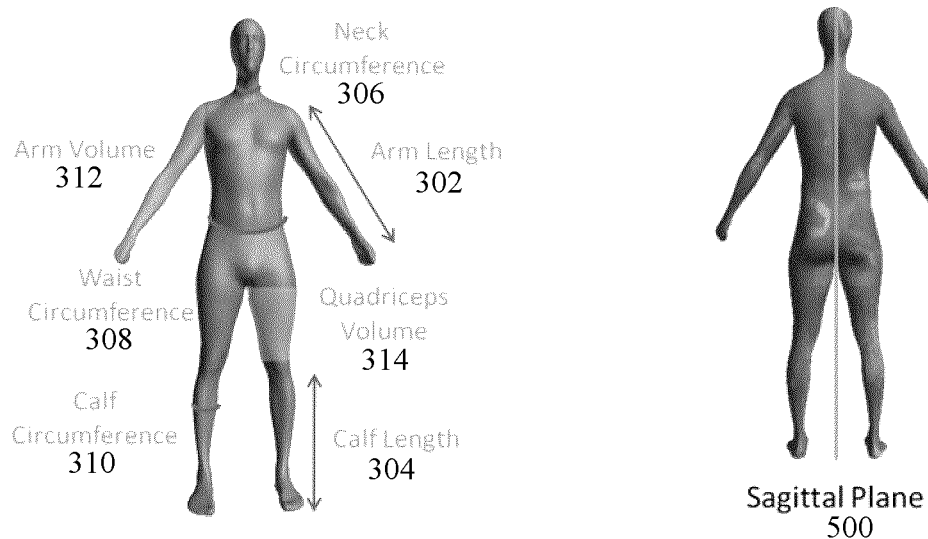
FIG. 3
FIG. 5
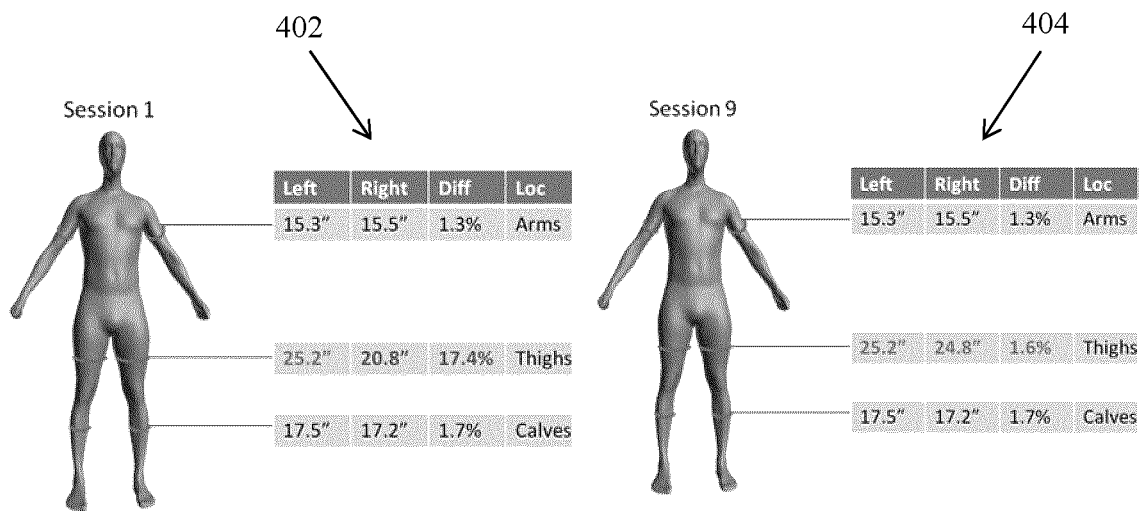
FIG. 4A
FIG. 4B

Transparent Outlined View of 3D Body Image

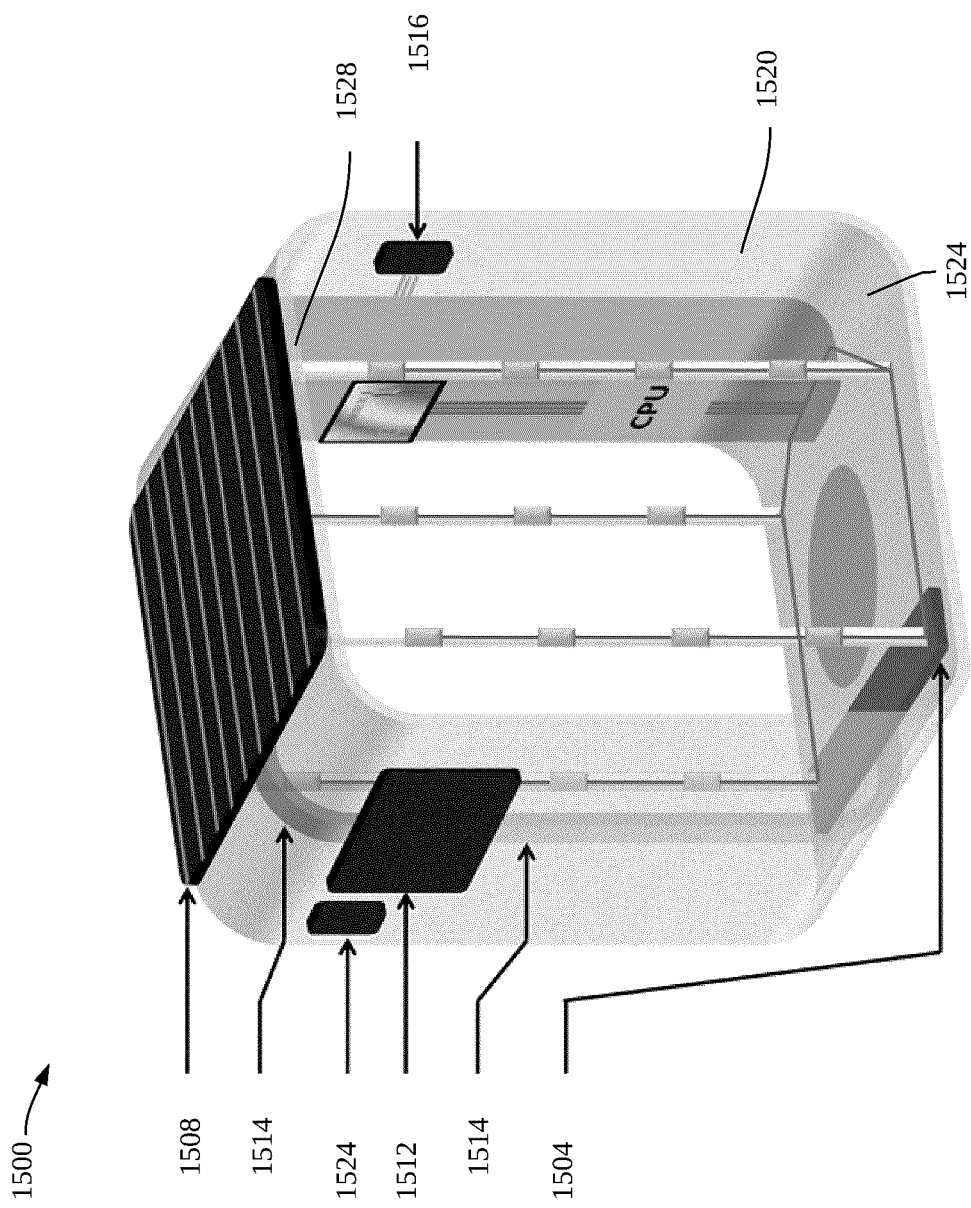

SYSTEM, METHOD AND KIT FOR 3D BODY IMAGING

RELATED PATENT APPLICATION

The present application is the U.S. National Stage of international application No. PCT/CA2018/050754, filed Jun. 21, 2018, which claims priority from U.S. provisional patent application No. 62/522,891, filed Jun. 21, 2017 and entitled "SYSTEM AND METHOD FOR 3D BODY SCANNING", the contents of each of which are hereby incorporated by reference in their entireties.

TECHNICAL FIELD

The technical field generally relates to 3D body imaging.

BACKGROUND 3D imaging has become the de facto standard for digitizing real world objects (e.g. shoes, compressors, brains, mapping, and planetary topology) across varying fields of interest (e.g. clothing and fashion, medical, oil and gas, geomatics, and gaming). The conversion of visual data into digital data has enabled innovative solutions in several fields of technology including Google's street view, 3D printing of a human heart, rapid prototyping, brain image analytics for neurological diseases, and the realism of video games like EA Sports' FIFA Football. While 3D imaging has had a strong impact on several industries, it is still limited as a solution for the common individual in relation to personalized health, wellness, fitness, medical state and rehabilitation.

SUMMARY

The present application describes a 3D body imaging system which focuses on innovative 3D imaging techniques particularly useful in health, wellness, fitness, medical and rehabilitation applications. The system includes a number of components, including a body imaging unit provided with sensors for acquiring 3D body data, and a processing server and database for processing and storing the acquired data, and for providing users access to personalized health, wellness, fitness, medical, and rehabilitation data derived therefrom.

According to one aspect, there is provided a kit for capturing a 3D image of a body of a user. The kit comprises a plurality of pillar segments being configurable between an assembled configuration and a disassembled configuration, in the assembled configuration, the pillar segments being joined to form at least one upstanding sensing pillar having an elongated body defining a vertical axis. The kit also comprises a plurality of sensors each defining a respective field of view and being configured to be supported on the elongated body of the at least one upstanding sensing pillar when formed and to be distributed along the vertical axis to have overlapping fields of view, the sensors being operable to capture image data of the body of the user.

According to another aspect, there is provided a system for capturing a 3D image of a user's body. The system comprises a plurality of sensing pillars positioned to surround the user's body and capture image data thereof from different perspectives. Each sensing pillar includes an elongated body extending along a vertical axis, said elongated body being formed from a plurality of assembled segments movable between an assembled configuration in which the segments are secured to one another to form the elongated body, and a disassembled configuration in which the segments are separated from one another, and a disassembled configuration in which the segments are separated from one another, and a plurality of sensors supported on the elongated body and distributed along the vertical axis with overlapping fields of view, the sensors being operable to capture image and feature data of the user's body. The system further includes at least one processing unit in communication with the sensing pillars, the processing unit being operable to receive the image data from the sensors and process the image data in order to form the 3D image of the user's body.

According to various kits and systems described herein, one or more solar panels are furthered configured for providing power to a plurality of electrical components of the kit other than the plurality of sensors.

According to various kits and systems described herein, at least two of the pillar segments configured to be joined to form one of the upstanding sensing pillar are detached from one another when in the disassembled configuration.

According to various kits and systems described herein, the sensors are detachable from the pillar segments.

According to various kits and systems described herein can further include at least one carrying case for enclosing and transporting the sensing pillars in the disassembled configuration.

According to various kits and systems described herein the at least one carrying case is configured for enclosing and transporting the plurality of sensors.

Various kits described herein further includes one or more solar panels are furthered configured for providing power to a plurality of electrical components of the kit other than the plurality of sensors receive the image data captured by the sensors and to process the image data to generate the 3D image of the body of the user.

According to various kits and systems described herein, the sensors are operable to capture feature data of the body of the use and processing unit is configured to enhance the 3D image of the body of the user based on the captured feature data.

According to various kits and systems described herein the processor unit is further configured to measure dimensions of the generated 3D image.

According to various kits and systems described herein the processing unit is further configured to generate a population model from 3D images of a plurality of different users' bodies.

According to various kits and systems described herein the processing unit is further configured to standardize and normalize a body position of the user in the generated 3D image.

According to various kits and systems described herein the processing unit is further configured to compare 3D images of the body of the user captured during separate imaging sessions.

According to various kits and systems described herein the processing unit is further configured to analyze the 3D image in order to identify physical traits and features indicative of a medical condition of the user.

Various kits and systems further includes a user interactive device being operable to be connected to the sensors and to receive instructions for operating the sensors.

Various kits and systems further include a wireless communication submodule configured for being in data communication with the processing unit and for transmitting one or more of the captured image data and the generated 3D image of the body of the user to an electronic device located remotely of the plurality of sensors.

Various kits and systems described herein further include a standing mat for supporting the user, the standing mat being placeable in proximity of the at least upstanding sensing pillar when formed and within the overlapping fields of view of the plurality of sensors.

Various kits and systems described herein further include comprising an enclosure sized to substantially enclose the at least one upstanding sensing pillar when formed and to receive the user.

According to various kits and systems described herein, the upstanding sensing pillar is sized to be positioned within an enclosure sized to substantially enclose the at least one upstanding sensing pillar and to receive the user.

Various kits and systems described herein further include a climate control subsystem operable to control one or more environmental conditions present within the enclosure and a thermostat operable to sense at least one environmental condition within the enclosure and to control the climate control subsystem to adjust the at least one environmental condition present in the enclosure to a predetermined setpoint.

Various kits and systems described herein further include a power storage unit for storing electrical energy for powering the plurality of sensors.

Various kits and systems described herein further include one or more solar panels configured for one or more of powering the plurality of sensors and charging the power storage unit.

According to various kits and systems described herein, the one or more solar panels are furthered configured for providing power to a plurality of electrical components of the kit other than the plurality of sensors.

According to yet another aspect, there is provided a method for capturing a 3D image of a user's body. The method includes a) capturing image data of the user's body from a plurality of different perspectives having overlapping fields of view, b) combining the image data to create a full 3D image of the user's body, c) repeating steps a) and b) for a plurality of different users and imaging sessions, d) combining the full 3D images created for the plurality of different users in order to create a model corresponding to a population of users and e) comparing the full 3D image of the user's body with the model in order to identify similarities or differences between the user's body and bodies in the modelled population.

Various methods described herein further include generating medical data using the 3D image of the user's body.

According to various methods described herein, generating medical data comprises using one or more of deep learning, machine learning, and artificial intelligence to generate one or more of a medical forecast, a medical risk assessment and a medical diagnostic based on one or more of the 3D image of the user's body, medical data and 3D body images generated during clinical trials.

Various methods described herein further include storing the medical data and the 3D body data of the user on a remote server, and linking said medical and 3D body data with an account associated with the user.

Various methods described herein further include analyzing a history of medical data and 3D body data linked with the account to track a progression of a medical condition.

According to various methods described herein, analyzing a history of medical data and 3D body data includes tracking a weight and height of the user.

These components can be implemented in a number of different ways in order to provide a robust system which is also easy and intuitive to operate.

BRIEF DESCRIPTION OF THE DRAWINGS

Embodiments will be described in greater detail with reference to the accompanying drawings, in which like reference numerals indicate like elements, and wherein:

FIG. 3 is a schematic illustrating subsets of body measurements which can be quantified by the 3D body imaging system, according to an embodiment.

FIGS. 4A and 4B are schematics illustrating changes in body measurements quantified by the 3D body imaging system in different sessions, in an embodiment where the 3D body imaging system is used to monitor progress in rehabilitation.

FIG. 5 is a schematic illustrating how body asymmetries can be identified using a 3D body image.

FIG. 15 illustrates a diagrammatic representation of an enhanced 3D body imaging unit for deployment in environmentally concerned, resources limited, and remote locations according to one embodiment.

DETAILED DESCRIPTION

Figure 1:
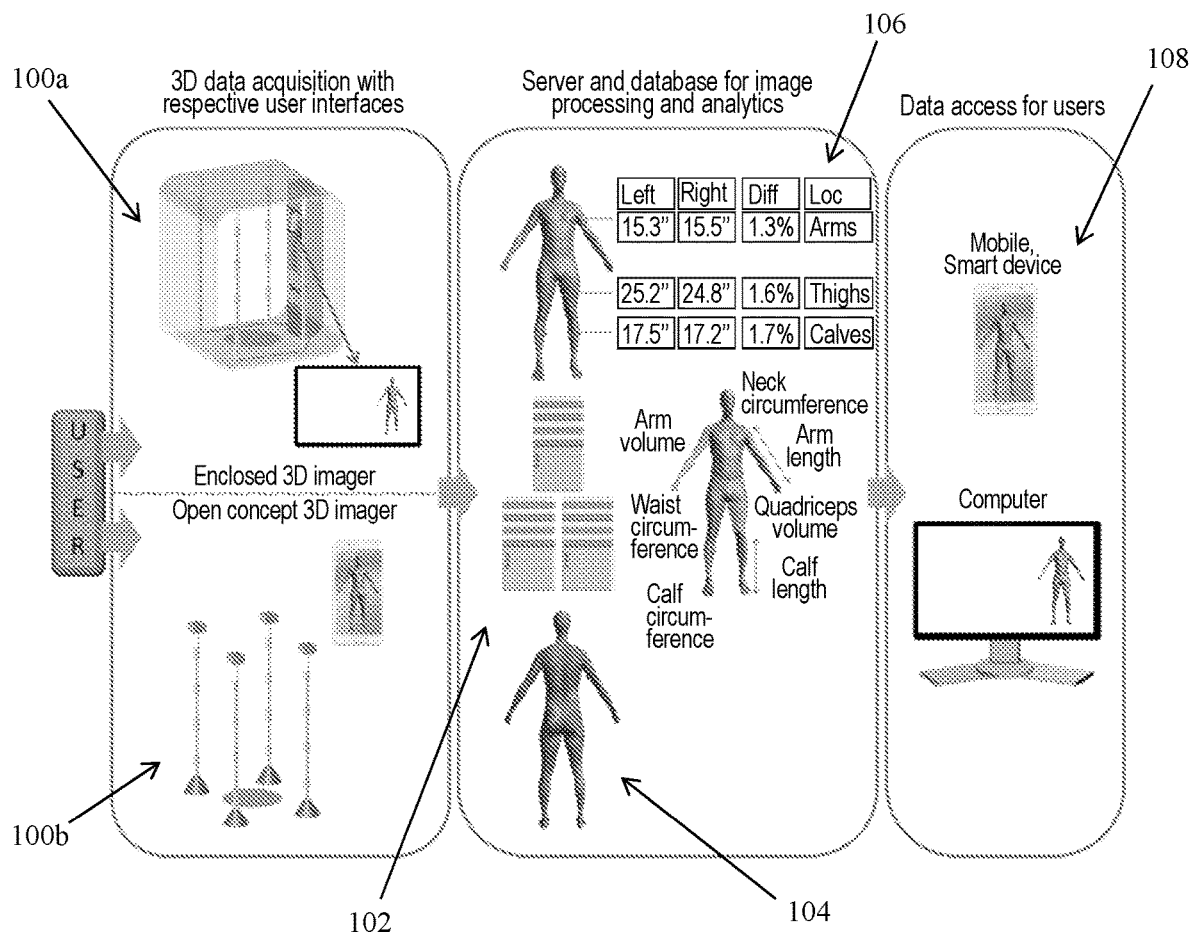
FIG. 1 is a schematic showing a general overview of the 3D body imaging system.

Various embodiments are described hereinafter with reference to the figures. It should be noted that the figures are not drawn to scale and that elements of similar structures or functions are represented by like reference numerals throughout the figures. It should also be noted that the figures are only intended to facilitate the description of the embodiments. They are not intended as an exhaustive description of the invention or as a limitation on the scope of the invention. In addition, an illustrated embodiment needs not have all the aspects or advantages shown. An aspect or an advantage described in conjunction with a particular embodiment is not necessarily limited to that embodiment and can be practiced in any other embodiments even if not so illustrated.

With reference to FIG. 1, a general overview of a 3D imaging system (ex: corresponding to an assembled kit) and associated method is provided. The technology allows a person or user to walk into an imaging unit 100a, 100b, interact with a user interface device (e.g. touch-screen monitor, keyboard, microphone for voice interaction, etc), and take a 3D image of themselves. The data acquired from the 3D imaging system can then be transferred to a server 102 for processing in order to produce a fully reconstructed 3D image of the person 104 and stored in a database. The 3D image 104 can be subsequently measured and analyzed 106 to quantify characteristics of the person's body. All data including body measurements, analytics, diagnostics, and assessments can be stored on the server in the database. Higher order analytics using the full database and statistical models can also performed to provide a person with health, wellness, fitness, medical and rehabilitation diagnostics and assessments like susceptibility to heart attacks, spinal and postural problems, and muscle rehabilitation progress. The analytics can be based on anatomical data and the relationship to health, wellness, fitness, medical and rehabilitation indicators (e.g. waist-hip ratio is a strong indicator of potential heart attacks, asymmetric anatomical structures are indicators of skeletal or musculoskeletal problems). The data stored in the database can be accessed by users, allowing them to view data through a secure online dashboard using any web environment (e.g. mobile, smart device, or computer) through a secure login 108.

A first step of the above-mentioned process involves generating a 3D image of a user's body, the 3D image corresponding to a digital representation of the shape of a user's body. The 3D image can be created, for example, by means of a 3D imaging unit. Although particular embodiments of 3D imaging units will be described in more detail hereinafter, it is understood that the term 3D imaging unit can encompass a wide range of different hardware configurations/assemblies which can acquire data to generate a 3D image of a user's body. Preferably, the 3D imaging unit includes a sensor or a plurality of sensors operable to capture surface images of a user's body from different perspectives.

Figure 2A:
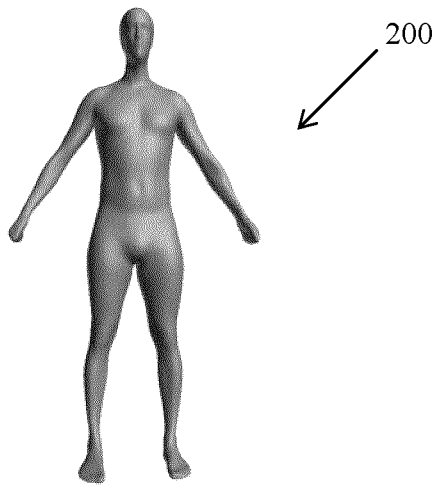
FIGS. 2A and 2B are various views of a fully reconstructed 3D image of a user generated using the 3D imaging unit.
Figure 2B:
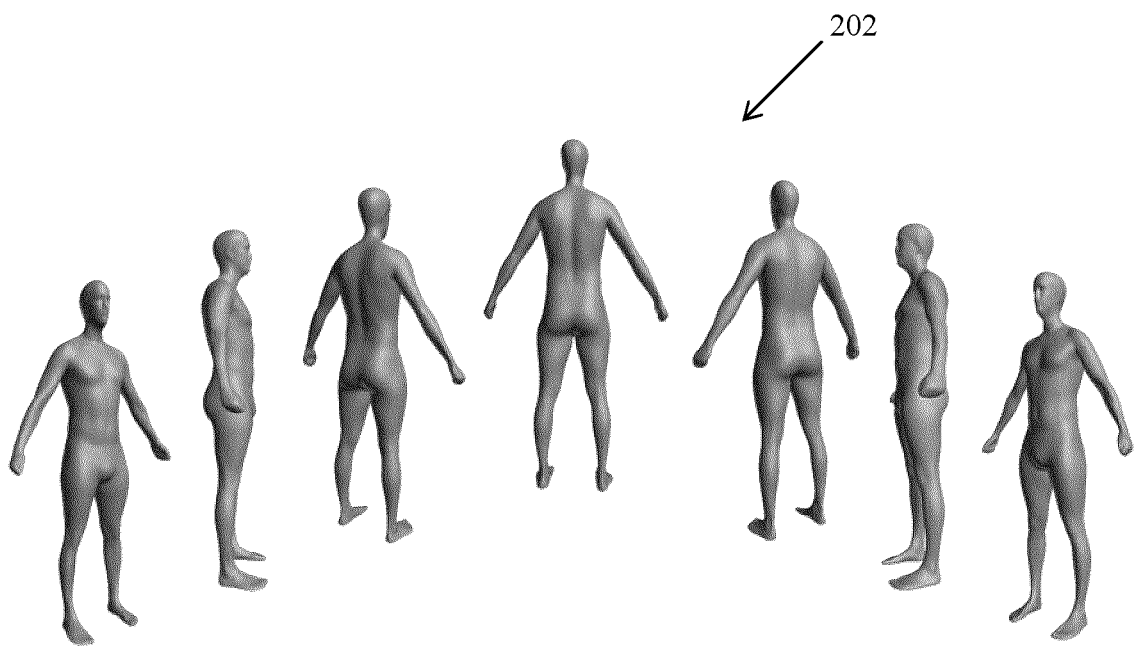

Image data captured by the 3D imaging unit is processed in order to produce a fully reconstructed 3D image of the user's body. For example, each of the sensors can capture 2D/3D images of different portions of the user's body from different perspectives, and these 2D/3D images can be combined in local or remote processing systems in order to build a full digital representation of the user's body in the form of a 3D image. In embodiments where the sensors capture surface images of the user's body, the 3D image can be constructed as shell/boundary representation 200 of the 3D surface of the user's body, as best illustrated in FIG. 2A. As shown in FIG. 2B, the generated 3D image is preferably a full 3D image in that it represents the surfaces of a full 360° of the user's body 202.

Processing the image data to build the 3D image can involve a number of image processing steps. First, images captured from each perspective are segmented. This involves delineating the object of interest (in this case the portion of the user's body that was in the sensors field of view) from all other objects in the image. Next, the images can be de-noised, for example by applying a statistical-based de-noising algorithm to remove outliers that do not belong to the object of interest. Next, the 3D image of the user's body can be reconstructed using the segmented and de-noised objects from each perspective. This can involve aligning and combining/assembling data from each perspective. The generated 3D image can include point cloud data. A mesh can be created using the aligned and reconstructed point cloud data, and the mesh can be further texturized, for example by painting the surface and adding lighting to produce an aesthetically pleasing 3D image. In some embodiments, generic textures can be applied to the mesh, such as the solid gold color shown in FIGS. 2A and 2B. In other embodiments, high-definition color images of the user's body or relating to features of the user's body like humidity, reflectivity, spectral emittance can be captured (for example using the same or different sensors in the 3D imaging unit), and these images can be applied to texture and enhance the content of the 3D image, thereby providing a true color representation of the user's body or features of the user's body for feature mapping and enhanced content for analytics.

In some embodiments, the image processing can further involve standardizing posture position. As will be explained hereinafter, the 3D image of the user's body can be compared with other 3D images of the user's body created during previous imaging sessions. However, it is unlikely that the user will have the exact same body position during two separate sessions, causing the resulting 3D images to be slightly different and making comparisons more difficult. In order to ensure accurate measurements over time, the generated 3D image is preferably digitally corrected in order to reposition the body into a standard posture position. As shown in FIGS. 2A and 2B, the standard position can be a straight posture, with legs approximately shoulder width apart, and arms extending on either side of the body at approximately 30°. However, in other embodiments, other positions are also possible, such as a T-pose (i.e. with arms extending at 90°). Standardizing posture in this fashion can allow differences between 3D images to be more easily measured, as the images can all be compared in a common reference frame.

In some embodiments, the image processing can involve classifying different parts of the 3D image. This can involve identifying and mapping different body parts in the image.

Classifying different parts in this fashion can be useful, for example, for making measurements and performing analyses on specific portions of the user's body using the 3D image. Different body parts that can be classified include appendages, individual muscles, muscle groups, etc., such as biceps, triceps, abdomen, forearm, head, feet, etc.

As can be appreciated, certain body parts may contain identifying characteristics, and that retaining 3D images with such data may present moral and legal privacy concerns. In order to protect the privacy of users, the captured 3D body data can be anonymized. For example, identifiable portions of a generated 3D image can be removed, obscured and/or replaced in order to ensure that the 3D image has no characteristics that can identify the user. For example, the user's face and/or head can be replaced with a generic head and/or face. Preferably, the digital head replacement maintains the realism of the 3D body image by eliminating transition lines between the head and body, ensuring an appropriate head size is used, and maintaining gender compliance through anatomical attributes (e.g. cranial differences between males and females) and features (e.g. hair). For example, this can involve mapping avatar heads from an avatar database on a set of data models to a 3D body image to anonymize the user's identity. This can prevent facial recognition software from determining a user's identity and provides a methodology for complying with privacy requirements. In some embodiments, sensitive areas of the user's body can also be removed and/or obscured.

Once the 3D image has been finalized, it can be stored on the system or sent to the cloud for subsequent processing and analysis. In some embodiments, prior to storing the 3D image, a quality control procedure can be performed in order to ensure that the 3D image and body images fulfill sensitivity and accuracy requirements. If these requirements are not met, the user can be notified and the system can request that the imaging steps be repeated.

Furthermore, quality control can include a number of steps. In implementation, the quality control ensures a person being imaged for a particular account is the actual person based on a matching metric and authentication credentials. The matching metric could include a correlation function or root mean square error. The current image can be aligned to the previous image using rigid body registration. The correlation between the two images can be calculated and a threshold can be used to determine a match. The difference between each point of the aligned images can be calculated, the root mean square can be determined, an average of the root mean square can be calculated, and a threshold can be used to determine a match as well. These two calculations can be used to measure the error between the two images which corresponds to the deviation from a true match. If the matching metric and authentication credentials determine that the user's images match then the image is accepted. If this is the user's first image or the system determines that there is no match, the following steps can be performed:

The image is compared against the other body images in the database for a match.

If a match is found in the database, an error is flagged and the person being imaged is asked to verify if they are actually the person that was found in the database. If the person verifies that it's their account, the image can be stored in the account linked to the found image in the database. If not the person can choose to continue with the imaging procedure and store the image in their account.

If no match is found, an error can be flagged and the person being imaged can be informed that they are not in the database and asked they would like to continue with the imaging procedure and store the image in their account or set up an account.

This system can also help with security in cases where a user's account has been compromised and attempts have been made to populate a user's account with non-conforming data.

In certain embodiments, the generated 3D image can be combined with other 3D images in order to create models. For example, 3D body images of all users can be combined in order to build population models of bodies and/or of certain classified body parts. Such models can, for example, represent the variability of body data across different populations. As can be appreciated, a 3D image captured for a particular user can be compared against the model in order to identify variances between the user's body and standard or average data of a given population. It is understood that models can be generated for an entire population, or any subgroups thereof. For example, models can be generated for populations grouped by sex, age, height, weight, size, etc. or any combination thereof. It is further understood that the models can have a temporal dimension, and can model standard changes in populations over time. In some embodiments, models can be generated for a population having a certain medical condition. This can be useful, for example, in monitoring the state of a user's body over time and identifying any medical conditions by comparing changes in the user's body with the population model for a certain disease type.

An example of a model for 3D body images can be described as a set of similar 3D images that are combined through averaging where high content like mean and variability are mapped onto the model itself. The general steps include identifying a group of interest (e.g. 30 year old males, pregnant females), registering each image that will form the model from its native space to a standard space, averaging all images that are transformed in the standard space, calculating the mean and variability of each point in the model, and difference between the point locations on the original native image and model (i.e. the change required to align the points on the native image to model). An image's native space represents the exact dimensions of the person that was imaged; this is the original acquired image. An image in standard space is the original native space image that is transformed to align with a body image that has a standard size and standard dimensions. The standard space body image is an image that is selected or created and is of high quality. Each acquired image is registered to the standard space image using a combination of linear and non-linear registration algorithms. The transformation parameters (i.e. matrices) required to transform each image from native space to standard space are calculated, stored, and applied during the registration process. This allows each point on each image to have a unique transformation parameter for alignment. These transformation parameters can be used to align an image from native to standard space and from standard to native space. This process allows every point on every image to be compared accurately and allow user data to be compared against populations. For example, a female user's 3D image could be compared against a female and male population model to determine gender.

Following the acquisition of a 3D body image, the 3D image can be measured and analyzed. The measurement and analysis of the captured 3D body image can allow for more meaningful information to be extracted from the image, for example to generate content-rich personalized information, diagnostics, and assessments for health, wellness, fitness, medical, and rehabilitation status.

In an embodiment, the 3D body image can be analyzed to provide anatomical measurements of different parts of a user's bodies. As illustrated in FIG. 3, various lengths can be measured, such as body height, shoulder-to-shoulder distance, upper torso length, forearm length, neck length, and patella-to-hip length. Various circumferences can also be measured, such as a circumference of the biceps, triceps, waist line, thighs, and calf circumference, as well as volumetric data, such as a full body, stomach, arms and quadriceps volume. For example, as shown in FIG. 3, analysis of the 3D image can allow for simultaneously measuring two distances (arm length 302 and calf length 304, for example in inches or centimeters), three circumferences (neck circumference 306, waist circumference 308 and calf circumference 310, for example in inches or centimeters), and two volumetric measurements (arm volume 312 and quadriceps volume 314, for example in cubic inches, cubic centimeters, or in liters). It is appreciated that other types of measurements can be acquired as well.

These measurements can be used for analytics purposes, for example to quantify changes in a user's body over time and/or to aid in the diagnosis of medical conditions. Preferably, method involves tracking each point on a user's body over time. This enables the detection of changes at every point on the body from one imaging session to the next. Tape measurements do not provide this degree of resolution (i.e. a tape measurement does not provide details on which part of the body increases or decreased in size. It is unable to determine whether the left or right pectoral muscle contributed to the changed in size). The present method for measurement tracking is capable of determining on a point-by-point basis which points contribute to changes in anatomical sizes (i.e. this method can tell what portion of the left or right pectoral muscle contributed to the overall change in chest size).

In some embodiments, the method can involve comparing images across time for users that have performed multiple imaging sessions as well as against other 3D body images and statistical models. For example, difference maps can be generated for each comparison to show the users where their anatomy has changed between imaging session and how their anatomy compares against other 3D images and statistical models (e.g. a statistical model for cancer). In fitness applications, the deviation could be an indication of muscle growth or fat reduction. In medical applications, the deviation could be an indication of body trauma resulting in inflammation. Comparing an individual's 3D body image to a statistical model like a cancer model can allow to inform the user of potential problems, provide early detection, and mitigate or prevent negative outcomes.

As can be appreciated, such comparisons can have practical applications in medical rehabilitation and diagnosis, and in athletic development. In some embodiments, the method can allow doctors, clinicians, and therapists to quantify rehabilitation progress by providing an accurate, robust, repeatable, reliable, and consistent way to measure and assess the progress. The above-described method can measure the same exact location on a subject at every imaging session and compare it against a gold standard (e.g. a healthy anatomical reference). This enables doctors, clinicians, and therapists to determine progress by accurately measuring the exact same location reliably and repeatedly over time (i.e. there is no significant variability in measurement location and/or method by the user) and provides insight (e.g. health forecasting and risk assessments) and recommendations on health.

FIGS. 4A and 4B illustrate the reliability and repeatability of the 3D body imaging method in rehabilitation. FIG. 4A shows the measurements 402 from a user's first imaging session for 3 paired locations: the left and right arms, thighs, and calves. In the current example, the user had a prolonged injury to the right thigh which resulted in atrophy and the measurements obtained from the 3D body imaging system shows a 17.4% difference between the healthy thigh and injured thigh. FIG. 4B shows the measurement 404 from the user's ninth imaging session for the same 3 paired locations. The user had received treatments and a training plan to rebuild the right thigh. The 3D body imaging system shows that the left thigh remained constant while the difference decreased to 1.6% demonstrating that the right thigh is responding well to the rehabilitation program. As explained above, the measurements obtained using the 3D body imaging system in session 1 and 9 are in the exact same location, and the method involves standardizing the measurement process for rehabilitation.

In other embodiments, the method can allow for the detection and diagnosis of certain medical conditions. As described above, models can be created from user populations with known medical conditions, and subsequently imaged users can have their bodies compared against the models to identify common body characteristic which may be indicative of said users having the medical conditions. Additionally/alternatively, 3D body images of users can be analyzed separately to identify known characteristics which are indicative of certain medical conditions.

For example, as illustrated in FIG. 5 the method can involve identifying asymmetries about the sagittal plane (i.e. the mid-plane shown as an orange line, 500). Asymmetries on the surface of the body can be attributed to injuries, disease, or an indicator of muscles and/or skeletal imbalance. These imbalances can lead to health issues. The present method can provide quantitative data on asymmetries and help users mitigate associated health issues. Moreover, this data can aid in the diagnosis of spinal conditions such as scoliosis or whiplash, and/or to aid chiropractors in monitoring spinal adjustments. As can be appreciated, the typical method for identifying and/or monitoring such conditions involves the use of x-rays, which can be quite harmful. The 3D imaging system described herein does not use x-rays, and can thus serve as a non-invasive way to track status and progress in spinal conditions. In some cases, the 3D imaging system can be used as an initial indicator to help doctors determine whether or not x-rays will be necessary.

It should be noted that a number of other medical conditions can also be identified and monitored using the 3D imaging system. For example, the 3D imaging system can be equipped to measure brown adipose tissue, which is an indicator of weight loss potential. The 3D imaging system can enable users to monitor their potential for weight loss and implement solutions to meet their weight loss goals. This can have a direct impact on other diseases (e.g. cardiovascular disease, arthritis, type 2 diabetes, stroke, hypertension, and types of cancer). The system can further measure obesity based on the 3D body image and relationship to Body Mass Index (BMI) and Brown Adipose Tissue; measure heart attack risk, by providing an accurate measurement of waist-hip ratio to determine a user's susceptibility to heart attacks; measure BMI based on a user's 3D body image data, Brown Adipose Tissue quantifications, and weight; measure inflammation based on a user's 3D body image data and spectral imaging sensors; and monitor pregnancy by determining anthropometric characteristics and features of a user's belly over the course of pregnancy, and relating them to the health of the baby.

The 3D body imaging system can enable users trying to achieve higher performance in their field of competition (e.g. athletes to build their body) to meet their performance needs. The 3D body imaging system can provide exact quantitative growth and symmetry measurements that can be used to determine power, flexibility, and strength. These measures can be compared against performance goals and milestones to ensure that a user is progressing towards their goals.

The system described herein can also create accurate digital models of each user that is imaged using the 3D body imaging system. Anthropomorphic data of each user can be stored. This data is the unique body signature of the user. It can provide many body characteristics that can be calculated from the body including measurements, shapes, ratios (e.g. upper to lower body), and anomalies (e.g. hip misalignment). This information can be modularized as an anthropomorphic module and can be used by customers (e.g. industries, companies, institutes, businesses, universities, governments) to add anthropomorphic intelligence (AI) to their solutions; thereby providing customized solutions rather than generalized solutions.

Figure 11A:
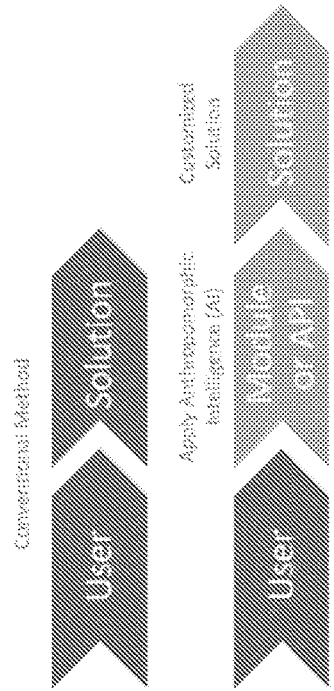
FIG. 11A is a schematic showing a comparison between a generalized solution and customized solution that uses an anthropomorphic module, according to an embodiment.
Figure 11C:
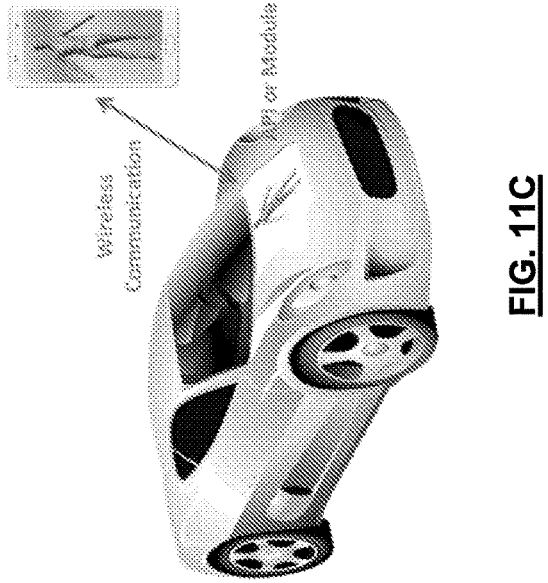
FIGS. 11B and 11C are schematics illustrating areas of application using an anthropomorphic module, according to possible embodiments.
Figure 11B:
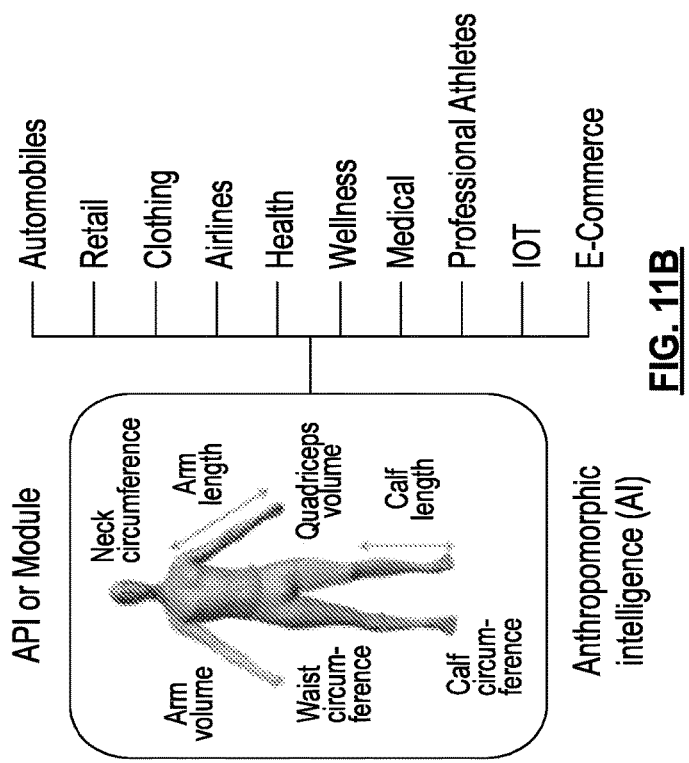

FIG. 11A shows a comparison between a generalized solution and customized solution that uses an anthropomorphic module. A typical use case for the anthropomorphic module would be applied towards applications that benefit from user specific body measurement data. FIG. 11B shows example areas of application. For example, car manufacturers can apply anthropomorphic customization modules to enable smart automobiles that set the driver's environment for the user (e.g. automobile seat and mirrors move into optimal position based on anatomical data). In this example, the car manufacturer would link with an anthropomorphic customization module. This can be through an application on the user's mobile phone. The module can provide the user's anthropomorphic data and the automobile can be set to the user's preferences. FIG. 11C shows an example application in an automobile. This has applications in autonomous vehicles where multiple users of varying shapes and sizes will share a common vehicle. Airline industries could apply this module to optimize seating (e.g. preventing several tall or wider people from being seated side-by-side) and balance weight distribution. Retail industry can use this module for custom clothing and proper fitting.

This module can be integrated as part of a mobile application. The application can contain user's anatomical data. Devices would integrate with the mobile application and receive anatomical data. Devices could be IOT enabled but are not limited to IOT enabled devices. The devices can automatically set conditions that are applicable based on anatomical data and user preference. The optional use of a GPS option allows the devices to set conditions prior to user's approach (e.g. car seat and mirrors move into optimal position based on anatomical data as the user approaches the automobile).

Figure 12B:
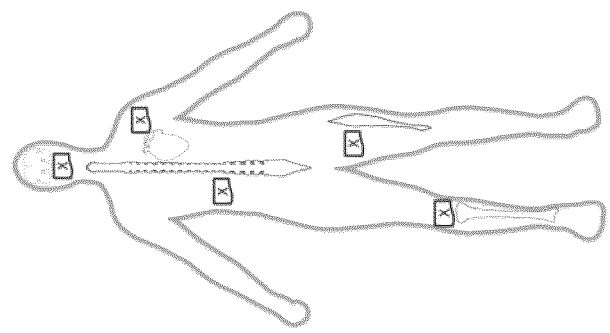
FIGS. 12A-12C are schematics illustrating mapping data to anatomical locations, according to an embodiment.
Figure 12A:
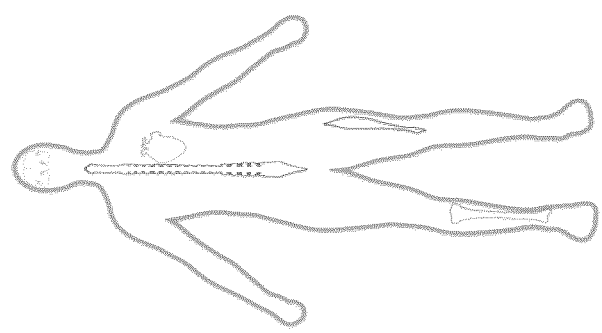
Figure 12C:
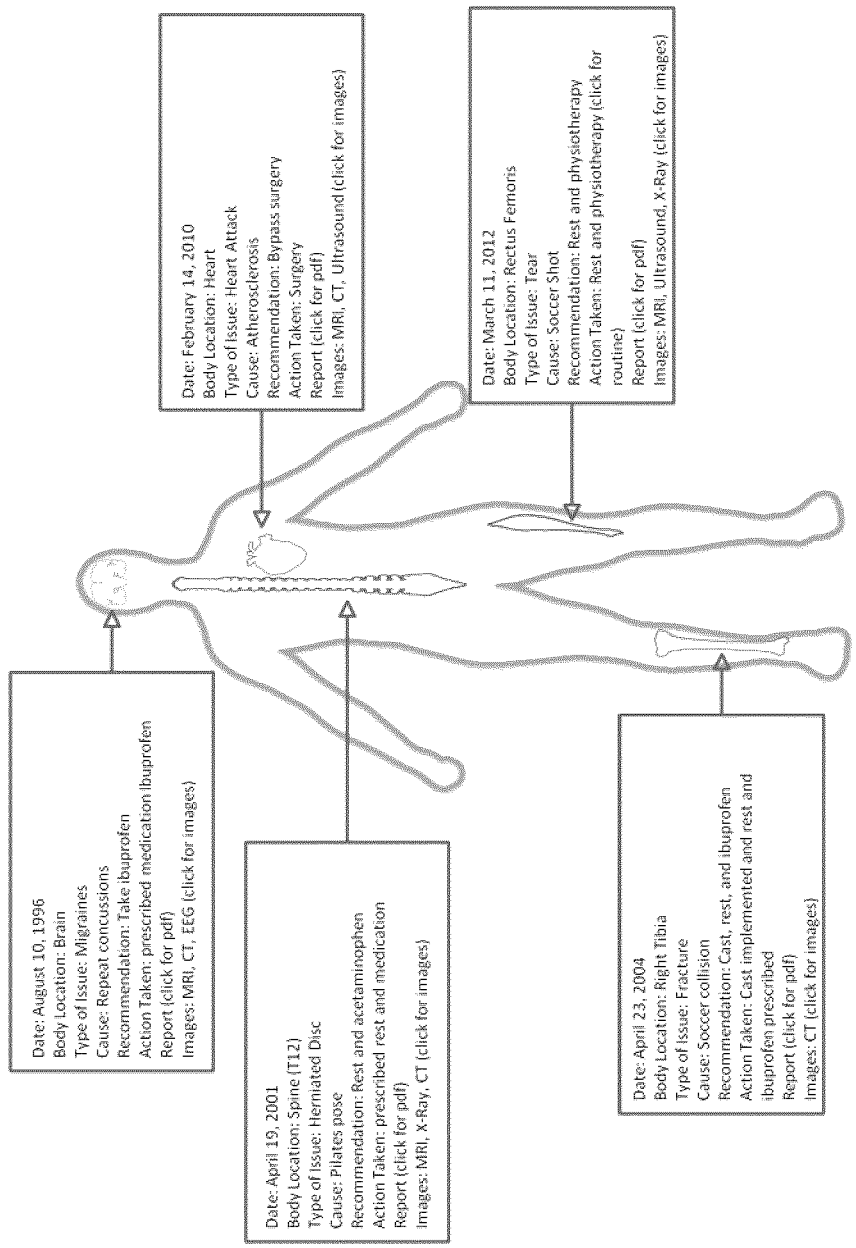

The 3D body imaging system can enable users (e.g. government health services, medical doctors, clinicians, hospitals, patients, individuals, rehabilitation institutes, therapists, chiropractors) to map the history of events that have occurred to a body. This can provide a complete visual record of many changes to the body. The anatomical mapping of changes to the body can include injuries, disease, surgeries, implants, prosthetics. The information for each anatomically mapped record can include high content data like date, location, images, type of issue, cause, recommendation, action taken, and reports (as shown in FIG. 12C). Use cases can include pre/post surgery (e.g. planning surgery, comparing expected and actual results), history of changes to predict and prevent future health issues, and visual representation and history for user's body changes. The anthropomorphic module can link with patient or user data that is acquired from the service providers (e.g. national healthcare databases, hospitals, therapists) and map the data to the respective anatomical location. Authenticated users can log in, view, and select locations where data is available, as shown in FIGS. 12A and 12B. Selected locations can expand to provide further details as shown in FIG. 12C. The data collected can be used to perform large volume health, medical, treatment, and rehabilitation analytics using machine learning. The digital health platform can consolidate body related data and information from various service providers in health, medical, treatment, rehabilitation (not limited to) and can map the information and data to the exact anatomical location on the user's 3D body image. If the user has not created a body image through the 3D body imaging device (i.e. the anatomical mapping system is agnostic to body images created by other methods), the user can import or link a body image created by a different method, use a standard model that is not anatomically accurate compared to the user's dimensions, or use the software to modify a generic model to reasonably reflect the accuracy of the user's body. In an embodiment, an anatomical database can be provided that describes the locations of all the components of a human body for all genders including musculoskeletal system, internal organs, lymphatic system, circulatory system, and integumentary system. The model based approach can be used to register the locations of all anatomical components from standard space (i.e. the coordinate space of the model) to the user's native space (i.e. the coordinate space of the user). A non-linear registration can be applied to align the dimensions of the model to the dimensions of the user's 3D body image. The transformation matrices can be stored and applied to the anatomical components (i.e. musculoskeletal system, internal organs, lymphatic system, circulatory system, and integumentary system) to bring them into alignment with the coordinate space and anatomical size of the user. This method can ensure the reliable mapping of the location of the anatomical component to each 3D image that is acquired. Furthermore, it can allow mapping of the consolidated body data and information to the user's body accurately.

Figure 6C:
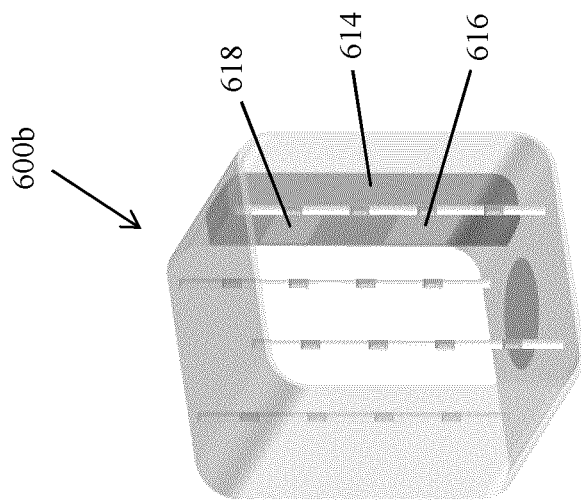
FIG. 6C is a partially transparent view of an enclosed 3D imaging unit showing the interior thereof, according to an embodiment in which the 3D imaging unit includes columns of sensors, a standing mat, a monitor, and a computer system.
Figure 6B:
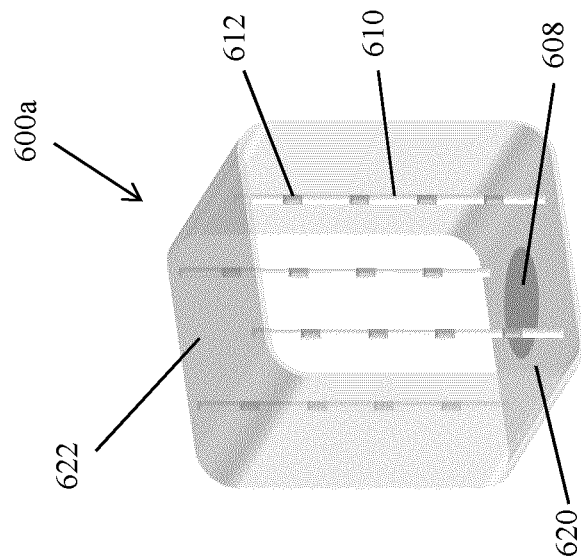
FIG. 6B is a partially transparent view of an enclosed 3D imaging unit showing the interior thereof, according to an embodiment in which the 3D imaging unit includes columns of sensors and a standing mat with weight and body mass index (BMI) scale and footprints for positioning.
Figure 6A:
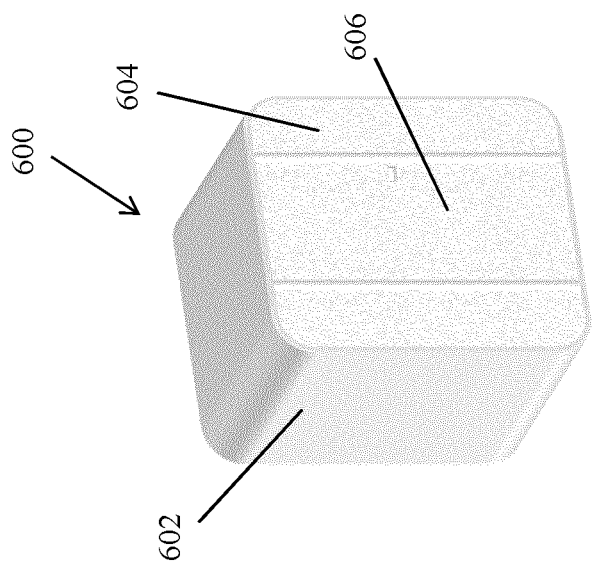
FIG. 6A is an exterior view of an enclosed 3D imaging unit according to an embodiment.

With reference now to FIGS. 6A-6C, embodiments of a 3D imaging unit are shown. The illustrated embodiments correspond to an enclosed 3D imaging unit, whereby the imaging sensors are positioned inside of an enclosure to provide users with privacy. As described elsewhere herein, various components of the 3D image unit may be provided in the form of a kit. Accordingly, these components can be assembled in order to form the 3D imaging unit. FIGS. 6A-6C are representative of an example embodiment in which components of a kit have been assembled to form the 3D image unit.

As shown in FIG. 6A, the enclosure 600 includes sidewalls 602 for blocking a view of the interior of the unit. Preferably, the sidewalls 602 are opaque so as to prevent light from escaping the enclosure. However, in some embodiments, some or all of the sidewalls can be partially opaque so as to allow light to enter the unit and aid in illuminating the interior without the need for a dedicated light source. For example, in the unit of FIG. 6A, one of the sidewalls 604 is made of frosted glass which allows light to enter the unit, while sufficiently diffusing light leaving the unit to maintain privacy.

The exterior of the imaging unit is preferably designed to be approachable and calming to users. In the present embodiment, the exterior includes curved soft edges and frosted acrylic glass. The unit further includes a door 606 for allowing entry, and is preferably provided with a lock which can be engaged and disengaged from the interior. Although not illustrated, hooks can be provided in the interior of the unit for allowing users to hang their clothing. Preferably, the hooks are placed in locations that do not block the line of sight between the user and the sensors capturing the 3D images. In this fashion, clothes hanging on the hooks would not compromise data during the acquisition process and negatively affect the final image.

Embodiments of the interior of the 3D imaging unit are better shown in FIGS. 6B and 6C. As best seen in FIG. 6B, a standing mat 608 is preferably provided in a central area of the 3D imaging unit. In the present embodiment, the standing mat 608 is a simple visual indicator for helping users to position themselves correctly when imaging their body. For example, the standing mat 608 can have a colored area which corresponds to an area which will be imaged. The standing mat 608 can further be provided with other visual cues, such as footprints, which can help users stand with their feet properly spaced apart, and which can help users to stand in a consistent position between several imaging sessions. Although in the present embodiment the standing mat 608 is merely a visual indicator, it is appreciated that in other embodiments, the mat can actively assist during the imaging process. For example, the mat can comprise a platform to support the user at a particular height, and/or can aid in controllably repositioning the user, for example by rotating or translating. Although in the present embodiment the standing mat 608 is a visual indicator, it is appreciated that in other embodiments, the mat can have an embedded weight/BMI scale to provide the weight and body mass index data of the user. The mat itself can be embedded into the floor of the 3D imaging system.

Sensors 612 are provided on the interior of the 3D imaging unit for capturing the 3D image of the user's body. Preferably, the sensors 612 are positioned to focus on a volume of interest corresponding to the standing mat. Preferably still, the sensors are stationary to reduce complexity by not requiring moving parts. However, in other embodiments, the sensors can move, for example to image a larger area with fewer sensors, possibly in combination with a moving platform. In the present embodiment, a plurality of stationary sensing pillars 610 (or columns) are positioned to surround the standing mat. In the present embodiment, the pillars 610 are fixed and cannot be repositioned. However, it is appreciated that in other embodiments, the pillars can be provided with a base and can be free-standing, allowing the pillars to be repositioned if necessary. In the present embodiment, each pillar comprises an elongated body extending vertically between a floor 620 and a ceiling 622 of the imaging unit, with a plurality of sensors 612 distributed there along. More particularly, each pillar 610 defines a respective vertical axis. As illustrated, the plurality of sensors 612 can be distributed amongst the pillars 610 and for each pillar 610, the set of sensors 612 attached to that pillar 610 can be positioned to be distributed along the vertical axis of that pillar 610.

Each sensor 612 has a respective field of view defining a three-dimensional space that is captured by that sensor 612. Preferably, the pillars 610 and the distribution of sensors 612 along each pillar are selected such that there are overlapping fields of view amongst the sensor 612. For example, adjacently located sensors 612 on a given pillar 610 can have overlapping fields of view. Similarly, sensors 612 positioned at the same height on two adjacently located pillars 610 can have overlapping fields of view. The pillars 610 and sensors 612 can be positioned to have overlapping fields of view such that the entire space to be occupied by the body of a user is covered by the aggregate of the fields of view of the sensors 612 of the 3D image unit. In an embodiment, an overlap of image data between sensors is maximized while ensuring full coverage of the object of interest being imaged.

As can be appreciated, in such configurations, no movement of the imaged object or sensors are necessary in order to obtain a full 3D image of the object. An image can thus be completed in a small period of time, thus reducing the risk of movement of the imaged object and/or of the sensors which could degrade the quality of the resulting 3D image, for example through blurring. As can be appreciated, by eliminating moving mechanical components in the present embodiment, data acquisition time and errors due to motion can be reduced. This can make the 3D body imaging device better suited for the medical and rehabilitation sector. Moreover, this design can limit the cost associated with mechanical failures and repairs. Furthermore, this design can enable elderly people, patients, and people with mobility issues (e.g. medical or sports injuries) to use the device given that there is no rotation/spinning of users during the imaging process, and given that users can be imaged at a faster rate.

In some embodiments, such as in the 3D imaging unit shown in FIG. 6C, a user interface can be provided for allowing users to interact with the imaging unit. In the embodiment of FIG. 6C, a computing unit 614 is housed inside the imaging unit, and comprises a touchscreen interface 618 for receiving input from a user inside the imaging unit. As can be appreciated, the touchscreen can process input from the user to initiate and/or control the imaging process. The touchscreen can also serve to allow the user to view resulting 3D images and/or analyses. In this configuration, the user can operate the 3D imaging unit and/or receive results therefrom from the privacy of the interior of the enclosed unit. For example, the user can enter the imaging unit, interact with the user interface, securely log into the system and follow on-screen instructions to create a 3D body image.

In other embodiments, different user interface configurations are also possible. For example, other input/output (I/O) devices can be provided, such as a keyboard, mouse, touchpad, LEDs, microphone (voice interaction), speakers, etc. In some embodiments, user interface devices can be alternatively or additionally provided on an exterior of the 3D imaging unit. Moreover, interfaces for operating the 3D imaging unit and for viewing results therefrom can be provided on separate devices, for example in the form of a native or web application running on a mobile device such as a smartphone or tablet.

In other embodiments, a single or plurality of sensors could be attached to a mobile phone, integrated within a mobile phone, or a combination thereof to enable a portable mobile version of the imaging device. Sensors could vary in type (e.g. depth, time of flight, photogrammetry, structured light, infrared, full spectrum, thermal sensors).

Figure 7:
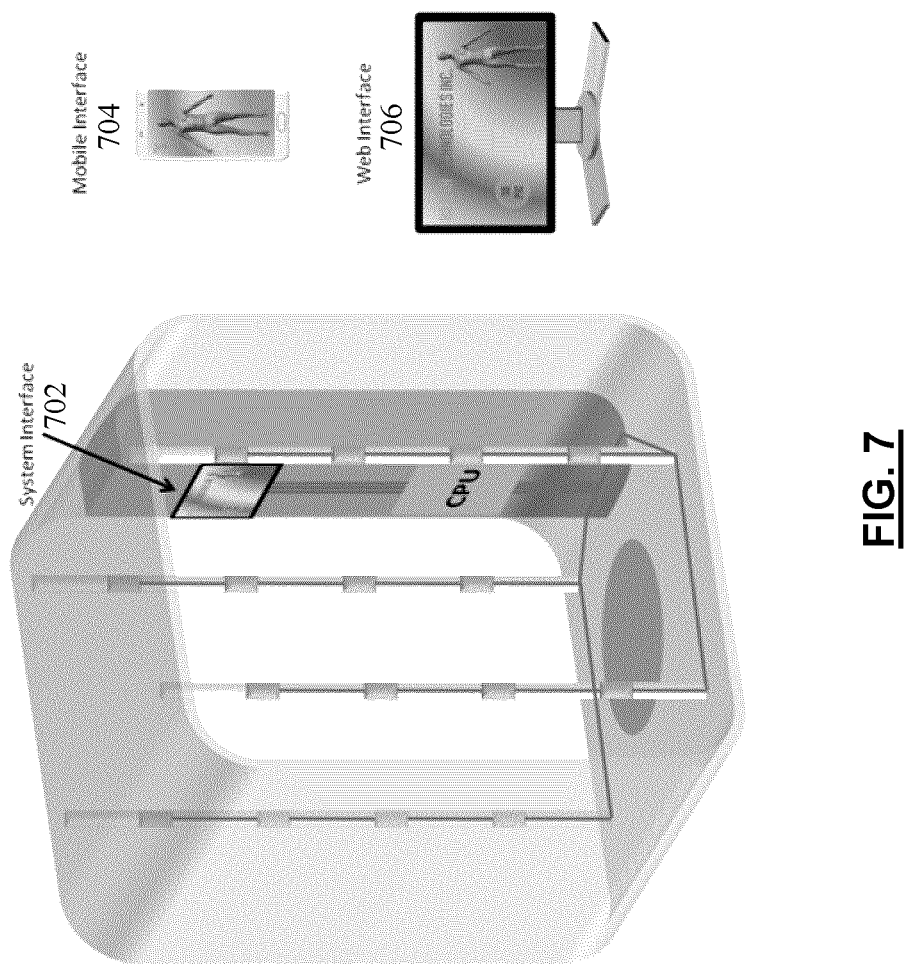
FIG. 7 is a schematic illustrating user interfaces for interacting with the 3D body imaging system, according to an embodiment.

As illustrated in FIG. 7, local and remote interfaces can be provided for interacting with the 3D imaging unit in different ways. A system interface 702 can be provided for allowing a user to interact with the 3D body imaging unit to acquire images. This interface can allow users to authenticate themselves, and to create their own 3D body image thereafter. The system interface 702 is generally a part of the 3D body imaging unit, however it can be provided on a separate device in some embodiments, such as on a mobile device with a network connection. Preferably, the system interface 702 provides instructions and guides the user through the image acquisition process.

Remote interfaces can be provided for allowing users to access results from the 3D imaging session, such as the 3D body image and measurements/analyses derived therefrom. For example, results and data can be provided to users on a personalized dashboard on the web or on a native application. Preferably, data from the 3D imaging session is stored centrally, for example on a cloud server, allowing users to access this data from any computer 706 or mobile device 704 with a network connection. Preferably still, the web interface is not physically connected to the 3D imaging unit.

In further embodiments, the local and remote interfaces can be used to authenticate users during the imaging session and/or after the imaging session in order to access the results. For example, in some embodiments, a QR code uniquely identifying the 3D imaging system and/or imaging session can be displayed on the local interface of the 3D imaging unit. Instead of having to provide username/password credentials to log in, a user can simply use their mobile device to take a picture of the QR code, for example using a special native application. This QR code can be recognized on the mobile device, and the mobile device can subsequently communicate with the imaging system to automatically provide it with user credentials pre-entered on the mobile device, such as mobile phone credentials or credentials from a linked social media account. It is appreciated that other technology can be used to facilitate the authentication of users, such as near-field communication (NFC), Bluetooth, etc. using mobile devices which support such technologies. In some embodiments, authentication can be done automatically using the sensors in the 3D imaging device. For example, the user could initiate an imaging session without first authenticating. The 3D body image captured can be analysed to extract information to personally identify the user (for example by recognizing certain body features). This information can be used as credentials to authenticate the user, and automatically associate the capture 3D image with the user's account. This procedure would be performed with the consent of the user and designed to conform with privacy regulations. The initial image would be registered to a user's account and all following images would be compared against all acquired datasets. The comparison algorithm that is applied to the datasets would have no link to the user data that is protected by privacy. Only body feature comparisons on anonymized data would be performed.

In some implementations, a user can apply a quick mobile-based login based on an authentication module, digital image on the monitor, and mobile application. The system can display a digital image on the screen for the user to interact with. The digital image can be a bar code, QR code, or other unique image. Each image on each imaging device is unique and specific to each device. The images for each machine are capable of changing to maintain security. The types of changes include automatic scheduling, per login (i.e. each time a login is performed, the image changes), and administrative (e.g. the head of security implementing a change because there is a need). The user applies the mobile application to authenticate themselves with the device. Through the application, the user simply takes a picture of the image on the screen. Given that the user is already authenticated on their phone (i.e. the system already has the user's validated authentication credentials) and the image displayed on the device is unique to the device, the mobile application is able to facilitate a quick authentication procedure. The authentication module on the servers validates the image provided from the user through the mobile application to the expected image that was provided by the servers and the users' phone authentication credentials. The authentication can also perform a proximity validation between the users' location based their mobile phone (e.g. GPS or WiFi data) to the device location (e.g. GPS, install location, IP address). The authentication system can have the option of asking the user to provide further information through the mobile application. This can include a personal pin or the device id displayed on the monitor. The mobile device based login can be an addition to the traditional user name and password login. This option can be provided on screen for logging in as well. Preferably, this can provide a better user experience through faster and secure authentication. In some implementations, blockchain is applied to ensure security, privacy, and interoperability of the data and system.

Different hardware configurations are possible to implement the 3D imaging unit. Such different configurations allow for deployment of the 3D imaging unit at different locations and for different use cases. However, it will be understood that the description provided herein with respect to the sensors, sensing pillar, pillar segments and computing unit of the 3D imaging unit are applicable to each of the different hardware configurations, as appropriate.

Figure 8A:
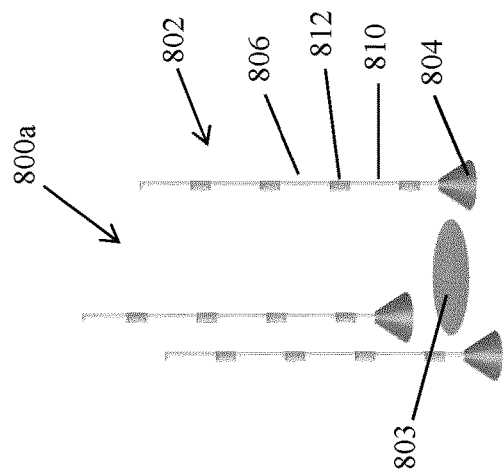
FIGS. 8A, 8B and 8C respectively show modular 3D imaging units comprising sensor pillars usable without a housing in an open concept, according to different embodiments in which the number of sensor pillars vary. The open concept can be adapted for outdoor/rural usage by encapsulating the system using a tent similar to camping material.
Figure 8B:
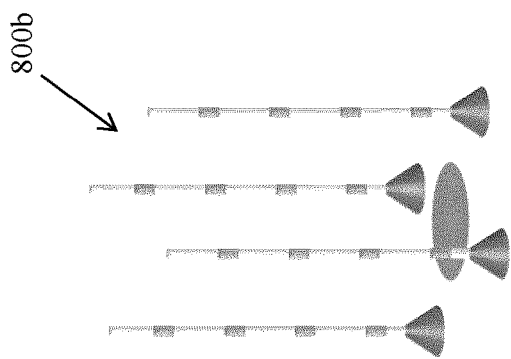
Figure 8C:
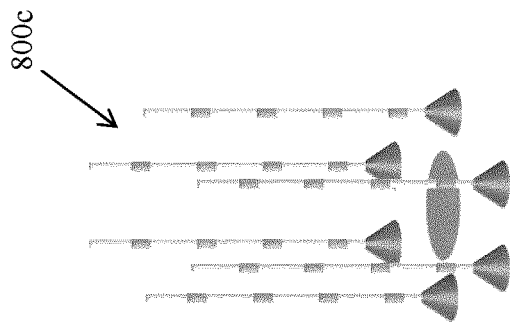

In some embodiments, for example as illustrated in FIGS. 8A-8C, the 3D imaging unit can be modular, allowing the pillars and sensors to be used without a housing unit. In this configuration, the imaging unit can be referred to as an open concept 3D imaging unit. In the illustrated embodiments, the 3D imaging unit 800 comprise a plurality of sensing pillars 802 positioned around an imaging area having a standing mat 803. The sensing pillars 802 are free standing and comprise a base 804 with an elongated body 806 extending therefrom. Preferably, the elongated body 806 can be separated from the base 804. In the present embodiment, the elongated body 806 comprises support segments 810 and sensor segments 812. Preferably, the support and sensor segments 810, 812 can be disassembled from one another. In some embodiments, components of the open concept 3D imaging unit 800 can be combined with the closed concept imaging unit 600, and vice-versa. The sensors 812 may be distributed amongst the sensing pillars 802 to have overlapping fields of view as described, for example, with reference to FIGS. 6A to 6C.

Figure 9A:
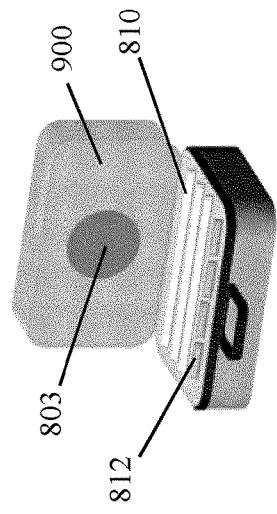
FIGS. 9A and 9B schematically illustrated a carrying case, and the modular 3D imaging units of FIGS. 8A-8C in a collapsed configuration for transporting therein.
Figure 9B:
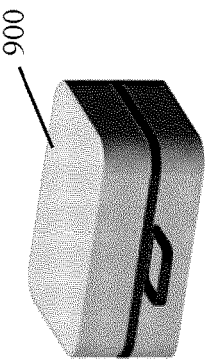

As can be appreciated, the modular configuration can allow the imaging unit to be transported more easily. For example, the pillars/sensors can be collapsed and/or disassembled (for example by separating base 804, support segments 810 and sensor segments 812), allowing the entire system to be transported in a compact carrying case 900 as illustrated in FIGS. 9A and 9B. A free-standing user interface, such as a tablet on a stand, can act as the system interface. Additionally/alternatively, the system interface can be provided as part of a native application on the user's own mobile device. As can be appreciated, such a configuration can provide the advantage of easier transport while potentially sacrificing privacy. The 3D imaging unit 800 illustrated in FIGS. 8A to 8C can be installed within an enclosure that is provided at the site where the 3D imaging unit 800 is being deployed. The enclosure can be a room within a building at the site.

However, in some embodiments, the system can include modular walls or expandable/collapsible tent-like structures which can be set up around the modular imaging unit to provide some privacy. The expandable/collapsible tent-like structure can have the shape and size as illustrated in FIGS. 6A to 6C.

The 3D imaging unit can be scalable, allowing for more or fewer sensors to be provided. As illustrated in FIGS. 8A-8C, more sensor pillars can be positioned around the imaging area in order to acquire data for larger objects and/or to increase the imaging resolution or level of detail. As can be appreciated, the number of sensor pillars can be increased or decreased to meet the needs for imaging objects of a variety of sizes. Preferably, the software controlling the image acquisition in the 3D imaging unit can recognize an increase or decrease in a total number of sensors, and manage the acquisition process accordingly.

Figure 13:
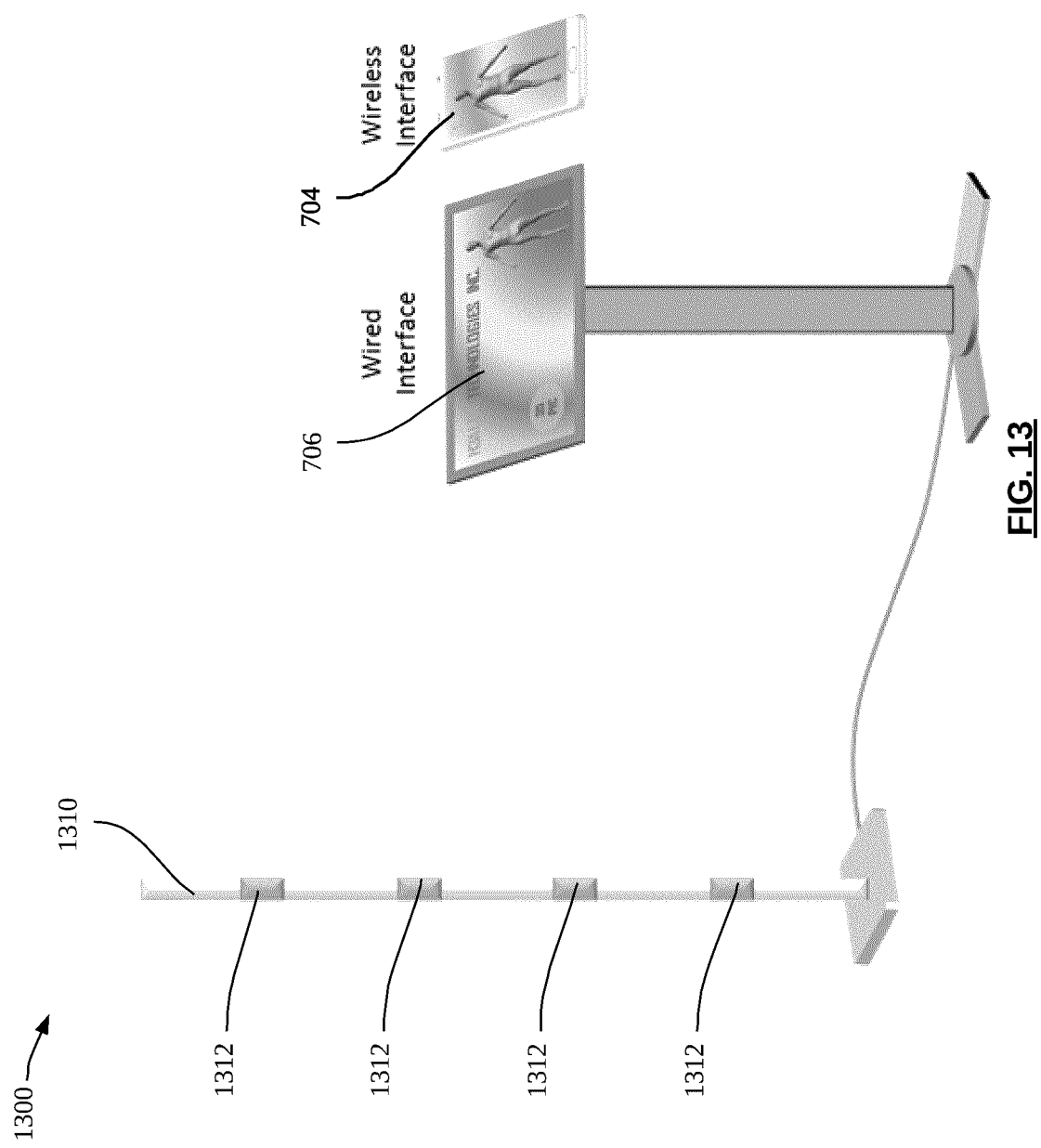
FIG. 13 shows a minimalist 3D imaging unit according to one embodiment.

In a minimalist embodiment, and as illustrated in FIG. 13, the 3D imaging unit 1300 includes one sensor pillar 1310 having a plurality of sensors 1312 positioned to be distributed along the vertical axis of the pillar 1310. Accordingly, either the sensor pillar 1310 or the user may be moved, such as being rotated, in order to capture a full 3D image of the user's body. In some cases, full 3D images covering a 360 degree view of the body are not necessary. Instead, 3D images for only a portion of the user's body is sufficient. The minimalist embodiment having a single sensor pillar illustrated FIG. 13 can be used to capture the partial image of the user's body. For example, the user is oriented so that the side of the body to be imaged is facing the single sensor pillar and the sensors are controlled to capture the images of that side of the body. Alternatively, the single sensor pillar can be rotated over a small angular distance (being less than a full circle) to capture the side of the body.

Moreover, in some embodiments, the types of sensors provided in the sensor pillars can vary according to different needs. For example, the sensor pillars can comprise sensors such as laser (e.g. depth sensors and time of flight sensors), digital images for photogrammetry, structured light, infrared, full spectrum, thermal, etc. and/or any combination thereof. Preferably, the sensors used are non-invasive in that they do not penetrate the body with harmful effects, like x-rays. Preferably still, the 3D body imaging system can apply multiple laser-based time-of-flight depth sensors to acquire point clouds from multiple locations. These point clouds can be processed to create digitized 3D body images. In addition to the point clouds that are obtained through these sensors, the unit can also be configured to capture high-definition digital RGB images. The system can apply the data from the high definition images to refine and increase the accuracy of the overall 3D body image and provide higher content (e.g. texture, skin moles, color variation, heat data). Preferably still, the system does not depend on either the point cloud data or high definition digital RGB data exclusively; the system should use either data set individually or in combination to produce high quality 3D body images. The 3D imaging unit can also be equipped to use infrared, full spectrum, thermal sensors and other to provide enhanced information, assessments, and diagnostics about their health, wellness, fitness, medical, and rehabilitation status. These sensors can be used to help build the 3D image, and/or to complement the 3D image by providing more information relating to aspects of the user's body other than its shape. Preferably, an interface between the sensors and the imaging unit is standardized, allowing for a "plug-and-play" type model, whereby a variety of different types of sensors can be connected to the 3D imaging unit without requiring changes to the image acquisition software. As can be appreciated, such a model can allow for simplified hardware upgrades, addition of new sensor types, or replacing defective or damaged sensors.

As mentioned hereinabove, the 3D imaging unit described herein can be provided in the form of a kit that includes one or more components described elsewhere herein. The components can be assembled in order to form the 3D imaging units described herein in accordance with various example embodiments. The kit includes the pillar segments 810 that are configurable between an assembled configuration and a disassembled configuration. In the assembled configuration, the plurality of pillar segments are joined to form at least one upstanding sensing pillar (610, 802). Each upstanding sensing pillar (610, 802) defines a respective vertical axis upon which sensors of the 3D imaging unit can be distributed. In the disassembled configuration, the pillar segments 810 are collapsed (ex: collapsed telescopically) and/or detached from one another. It will be appreciated that transportation of the 3D imaging unit can be facilitated from the segments 810 being in the disassembled configuration. For example, the pillar segments can be placed in one or more carrying cases 900 as described herein with reference to FIGS. 9A and 9B.

The kit also includes the sensors (612, 812). As described elsewhere herein, the sensors 812 are positioned to be distributed along the vertical axis of the sensing pillars 802 when the pillars 802 are formed from the pillar segments 810 being in the assembled configuration. The sensors (612, 812) can be pre-attached or permanently attached to the pillar segments 810. Alternatively, the sensors 812 can be detachable from the pillar segments 810, which may also facilitate transportation. For example, and as illustrated in FIG. 9A, the sensors 812 can be carried within the one or more carrying cases 900 when detached from the pillar segments 810.

The kit may also include the standing mat (608, 803). During assembly of the kit to form the 3D imaging unit, the formed sensing pillars (610, 802), sensors 812, and standing mat (608, 803) are appropriately positioned such that a user standing on the sensing mat (608, 803) is covered by the overlapping fields of view of the sensors 812. That is, the standing mat (608, 803) is placeable in proximity of the one or more upstanding sensing pillars (when formed) and within the overlapping fields of view of the plurality of sensors. When disassembled, the standing mat (608, 803) can also be placed within the carrying case 900, as illustrated in FIG. 9A.

The kit may also include the computing unit (614, 1004) for processing the captured image data of the body of the user. The computing unit can carry out various forms of processing, as described elsewhere herein.

The kit may also include the enclosure 602, which may be an expandable/collapsible tent-like structure for facilitating transportation.

3D imaging systems and kits described herein according to various example embodiments can be particularly well-suited for temporary deployment and/or deployment at a remote location.

"Remote location" herein refers to a location where various infrastructure services are not available. For example, the remote location can be a location that is not connected to the power grid, in which case electricity must be generated locally to power electrical components at the remote location. The remote location may also be a location that is not connected to a wired wide area data network, for example, for providing an Internet connection. It will be appreciated that services, such as medical and health services, that are typically available in more developed areas are often not readily available at the remote location.

It will be appreciated that the capability to disassemble the pillar segments 810 into a disassembled configuration allows for easy transportation of the segments to the remote location. The modularity of the kit/system also allows for adapting the components according to the requirements of the analysis to be performed at the remote site. As described above, there are a number of different steps involved in the capturing of image data, building a 3D image of a user's body, analyzing and measuring the 3D image, and presenting the captured and analyzed data to a user. As can be appreciated, depending on the hardware configuration, some or all of these steps can be performed locally on the 3D imaging unit, whereas in other embodiments certain steps can be offloaded to a remote server.

Figure 10B:
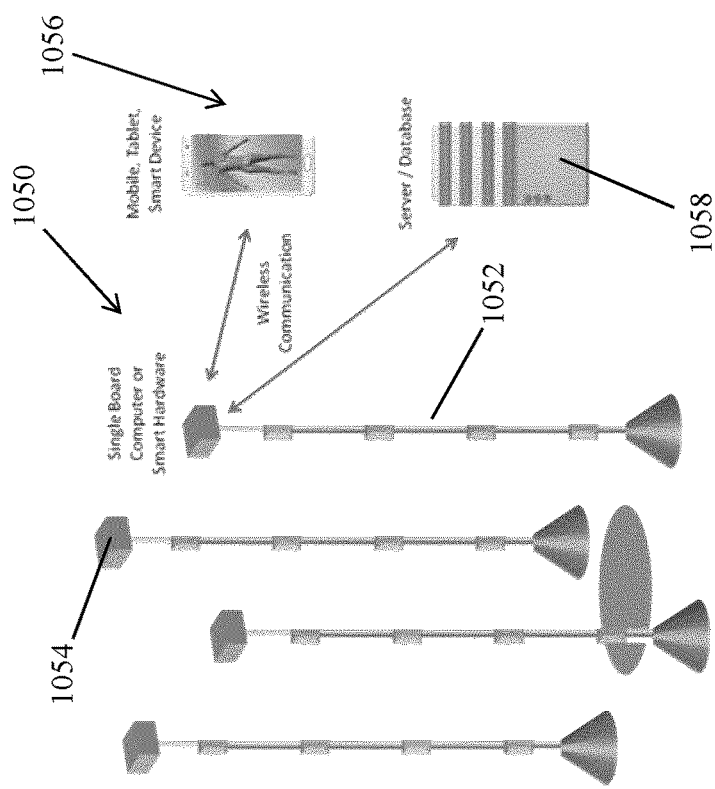
FIGS. 10A and 10B are schematics respectively illustrating hardware configurations for enclosed and open concept 3D body imaging units, according to respective embodiments.
Figure 10A:
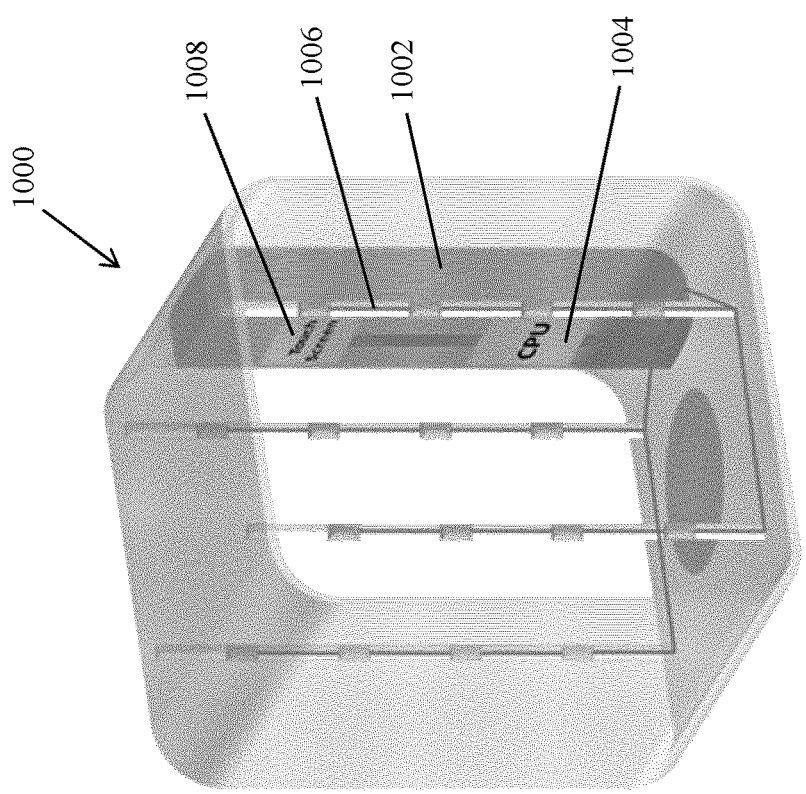

With reference now to FIG. 10A, an exemplary hardware configuration is shown for an enclosed 3D body imaging unit 1000. The imaging unit comprises a computing unit 1002 provided in an interior thereof. The computing unit comprises a processor 1004 (such as a CPU, application-specific integrated circuit (ASIC), or other such components) in communication with the sensor pillars 1006 and with a touch screen 1008, and can be further provided with a communications module (including connections such as WiFi, mobile, satellite, Bluetooth, Bluetooth LE, Ethernet, Swarm Intelligence, HDMI, USB, eSATA, etc.) for communicating with other devices over local or remote networks. In this embodiment, the CPU controls all aspects of the data acquisition process. For example, the CPU can control capturing images of the user's body using the various sensors (for example by setting the acquisition timing of the sensors, triggering the sensors to acquire data, etc.), and combining these images form the full 3D image of the user's body. The full 3D image can then be transferred to a centralized remote server, via the communications module, for measurement and analysis, and for storage in a database so that the data can be subsequently accessed by a user. In other embodiments, however, the CPU can perform more or fewer steps of the process. For example, the CPU could simply operate the sensors to capture images, and send the images to a remote server for creating the full 3D body image.

FIG. 10B shows an exemplary hardware configuration for an open concept 3D body imaging unit 1050. In this embodiment, each sensor pillar 1052 is provided with its own computing unit 1054, such as a single board computer (e.g. Raspberry Pi, HummingBoard, BeagleBoard, etc.) or customizable circuit boards (e.g. application-specific integrated circuits (ASIC), complex programmable logic devices (CPLD), field-programmable gate arrays (FPGA), programmable logic device (PLD)), that can communicate wirelessly to a smart device 1056 (such as a mobile phone, or tablet), or directly with a central server 1058. In this embodiment, the smart device can act as the user interface and/or can serve to operate the sensors in order to capture images of the user's body using the sensors, and upload the images to a remote server for further processing.

Data acquired can be analyzed and stored centrally, for example on a cloud server. Preferably, bank level security is applied to ensure the safeguard of the data. The cloud system can consist of a database data centre and server to store and process the data respectively. The database can store all data (e.g. 3D image data, business logic, analytics, diagnostics, and assessments), and each user can access their data from the database through a web or mobile interface after authentication. Preferably, the server runs the image processing software on all data and performs analytics and diagnostics (e.g. medical, physical, health, wellness, etc.). One embodiment is that the analytics and diagnostics is performed using a computer learning approach (e.g. deep learning, machine learning, and artificial intelligence (AI)). Data that is received from 3D imaging unit can be automatically screened for viruses, spyware, and malware. The data can then be automatically processed and stored in the database.

Figure 14A:
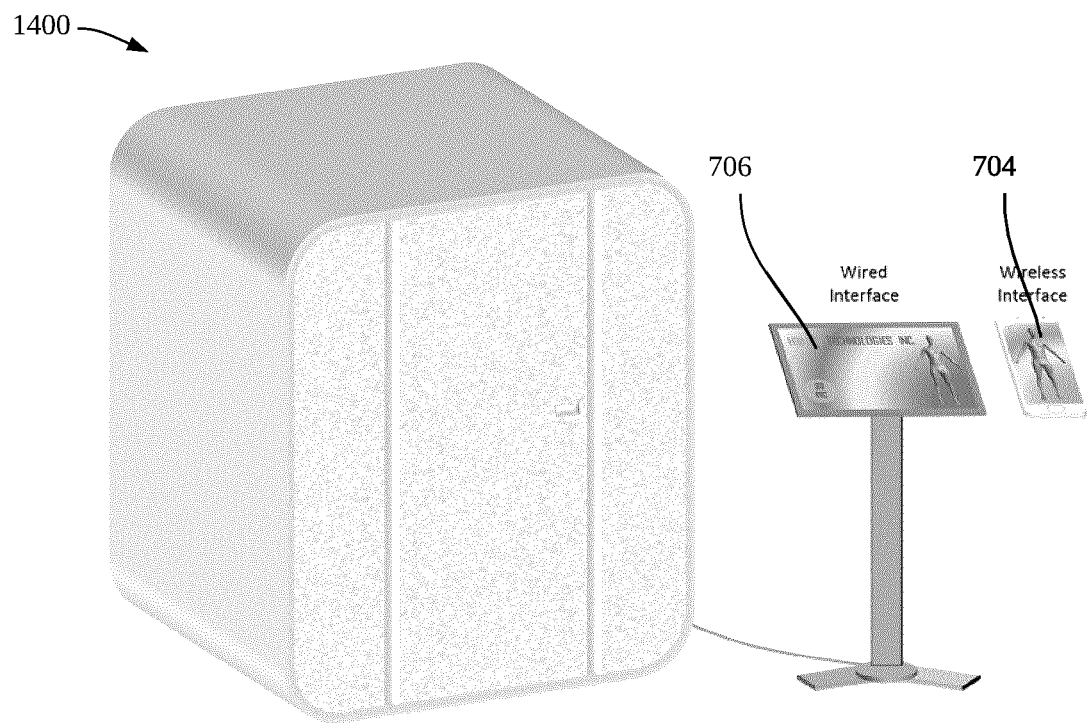
FIGS. 14A and 14B illustrate a hardware configuration of a 3D body imaging unit 1400 that may be suitable for environments where an operator manages the imaging for the user being imaged.

FIG. 14A illustrates an exemplary hardware configuration of a 3D body imaging unit 1400 that may be suitable for a deployment at a remote location. A computer 706 or mobile device 704 is provided to be in close range communication with the 3D imaging unit, such as the sensors and/or computing unit thereof. Furthermore, some processing of the captured 3D data is performed by the computing unit, computer 706 and/or mobile device 704 to obtain and generate the full 3D image of the user's body. For example, the computer 706 can be in data communication with the computing unit of the 3D body imaging unit 1400 via a wired connection or over a close-range wireless communication.

Figure 14B:
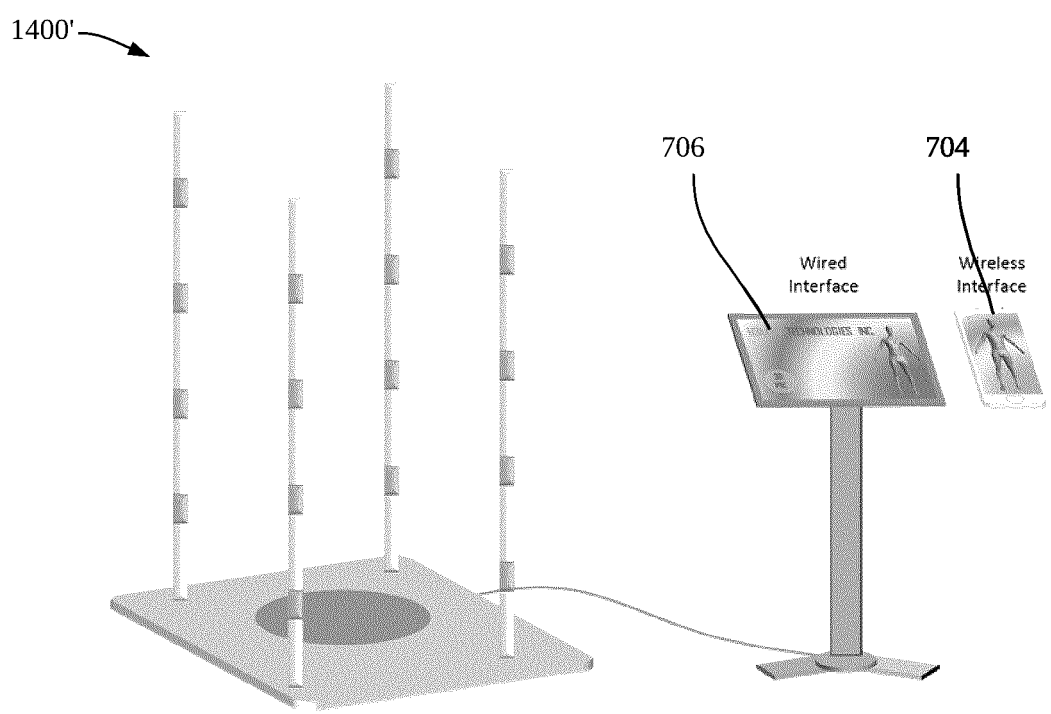

The hardware configuration of FIGS. 14A and 14B can be suitable for operational environments where an operator manages the imaging for users being imaged. This may be suitable for users that have functional disabilities that prevent them from imaging themselves. This may also be suitable for clinical environments where it is preferred that health professionals manage the imaging. It will be appreciated that the computer 706 and/or mobile device 704 are illustrated in FIGS. 14A and 14B to be out of reach from a user standing on the standing mat. Accordingly, the user is not expected to operate the computer 706 and/or mobile device 704 to control the sensors that capture images of the body. Instead, another operator operates these devices. It will be appreciated that the operator can control the sensors without himself or herself being captured by the sensors.

FIG. 14B illustrates an open concept body imaging unit 1400' that is equivalent to the hardware configuration illustrated in FIG. 14A, but without the enclosure. The computer 706 and mobile device 704 can be used to perform the imaging sessions for the user. The computer and mobile device may also be used to generate the 3D image of the user's body locally and provide accessibility to view the data.

It will be understood that the hardware configuration illustrated in FIGS. 14A and 14B is suitable for deployment at any location.

Referring now to FIG. 15, therein illustrated is a diagrammatic representation of an enhanced 3D body imaging unit 1500 according to an example embodiment. The enhanced 3D body imaging unit 1500 includes additional functionalities that aid capture and generating of 3D images of users' bodies and/or deployment of the 3D body imaging unit 1500. It will be understood that while the hardware configuration illustrated in FIG. 15 has a plurality of additional functionalities, various exemplary embodiments of the enhanced 3D body imaging unit 1500 may only have a subset of these functionalities.

The enhanced 3D body imaging unit 1500 may include as one of its additional functionalities a power storage unit 1504 (ex: one or more battery cells) that is operable for storing electrical energy. The electrical energy can be used to power one or more electrical components of the enhanced 3D body imaging unit 1500. For example, the power storage unit 1504 can provide electrical energy to power the plurality of sensors 812.

The enhanced 3D body imaging unit 1500 may also include as one of its additional functionalities one or more solar panels 1508 that are operable to receive light (ex: sunlight) and to convert the received sunlight to electrical energy. The electrical energy generated by the solar panels 1508 may be used to power the plurality of sensors (612, 812, 1312) and/or to charge the power storage unit 1504. The generated electrical energy may also be used to power other electrical components of the 3D body imaging unit 1500.

The enhanced 3D body imaging unit 1500 may also include as one its additional functionalities a climate control subsystem 1512 and a thermostat 1516. The climate control subsystem 1512 is operable to control one or more environmental conditions present within an enclosure or room in which the sensors (612, 812, 1312) and sensing mat (608, 803) are installed. For example, and as illustrated in FIG. 15, a plurality of cables and ventilation ducts 1514 can be connected with the climate control subsystem 1512 to vent cooled or heated air into the enclosure or room. The at least one environmental condition can include one or more of temperature, humidity and atmospheric pressure. Accordingly, the climate control subsystem 1512 can include one or modules that provides heating/cooling (ex: air conditioner and heater), and humidity control (ex: humidifier/dehumidifier).

The enhanced 3D body imaging unit 1500 may further include a thermostat 1516 that is operable to sense at least one environmental condition within the enclosure or room and to control the climate control subsystem to adjust the at least one environmental condition present in the enclosure or room to a predetermined setpoint. The thermostat 1516 can be operable to measure one or more of temperature, humidity and atmospheric pressure within the enclosure or room. Accordingly, it will be understood that the thermostat 1516 is not limited to only measuring temperature, but can also be used to measure other environmental conditions. The predetermined setpoint can define an operational range for each of one or more environmental conditions that ensure consistence in the imaging of a user's body. The operational range is chosen to limit measurement error and variability in imaging the user's body. For example, it was observed that ensuring consistent operating conditions is especially important for measuring certain health metrics, such as thermal data.

FIG. 15 illustrates an enhanced 3D body imaging unit 1500 having an enclosure 1520. The additional functionalities can be located within or on the enclosure 1520. For example, and as illustrated, the power storage unit 1504 may be embedded within a floor portion 1524 of the enclosure 1520. The solar panels 1504 may be installed over a top surface of the top portion 1528 of the enclosure 1520. The thermostat 1516 is installed inside the enclosure 1520. The climate control subsystem 1512 may be installed over an outer surface of the enclosure 1520, such as on a sidewall thereof. The cables and ventilation ducts 1514 may extend over an interior surface of the enclosure 1520.

Figure 16:
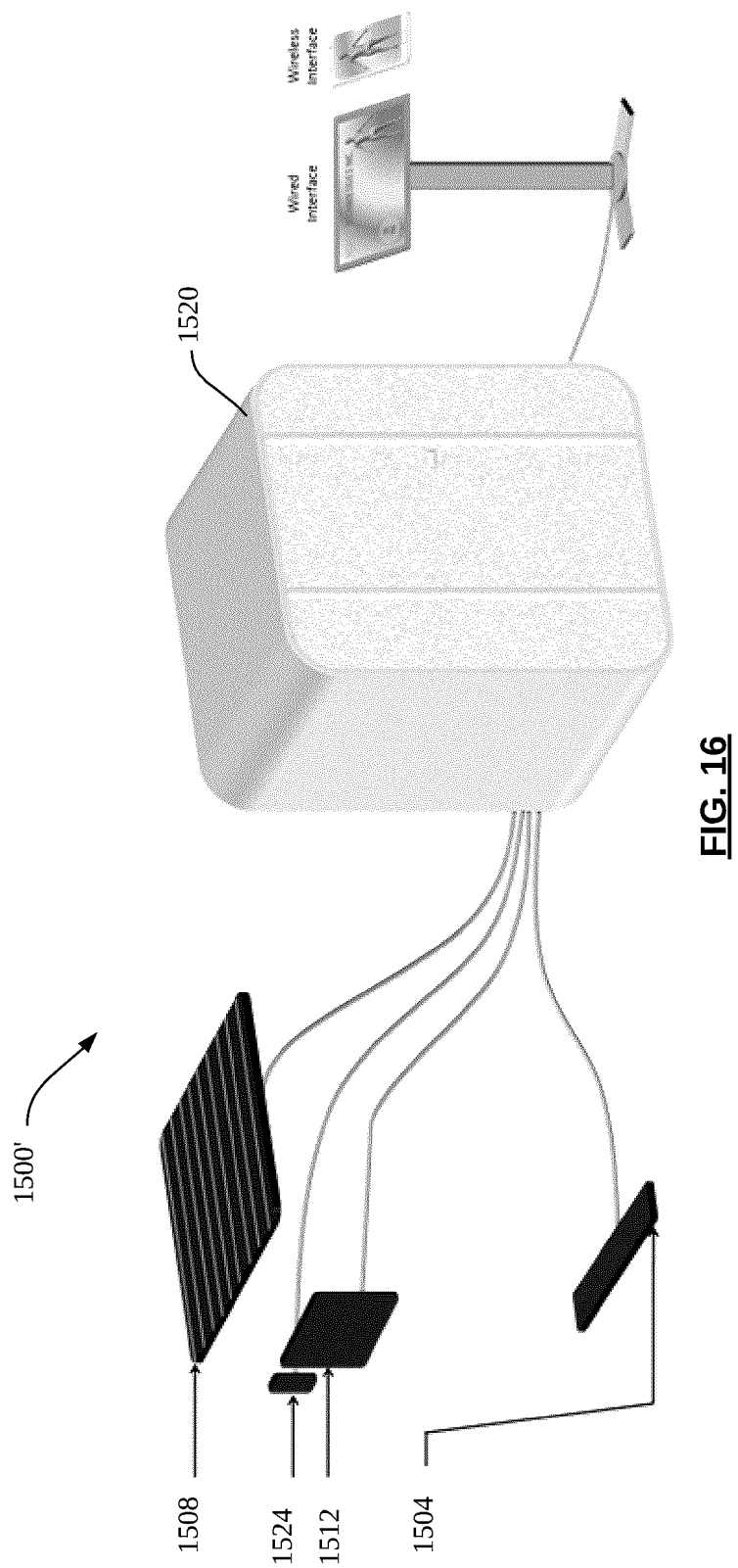
FIG. 16 illustrates a diagrammatic representation of an enhanced 3D body imaging unit according to another embodiment.

FIG. 16 illustrates an enhanced 3D body imaging unit 1500' having an enclosure 1520 but in which one or more components providing the additional functionalities are external to the enclosure 1520. The components can be connected to the enclosure 1520 and/or components inside the enclosure 1520 (ex: sensors and other electrical components) via suitable cabling and/or ducting. One or more of the components providing the additional functionalities (ex: power storage unit 1504, solar panels 1508, climate control subsystem 1512) may be located externally to the enclosure 1520 to improve performance thereof. For example, a power storage unit 1504 having a larger energy storage capacity can be provided. Similarly, solar panels 1508 can be located at locations that allow capture greater amounts of sunlight.

Figure 17:
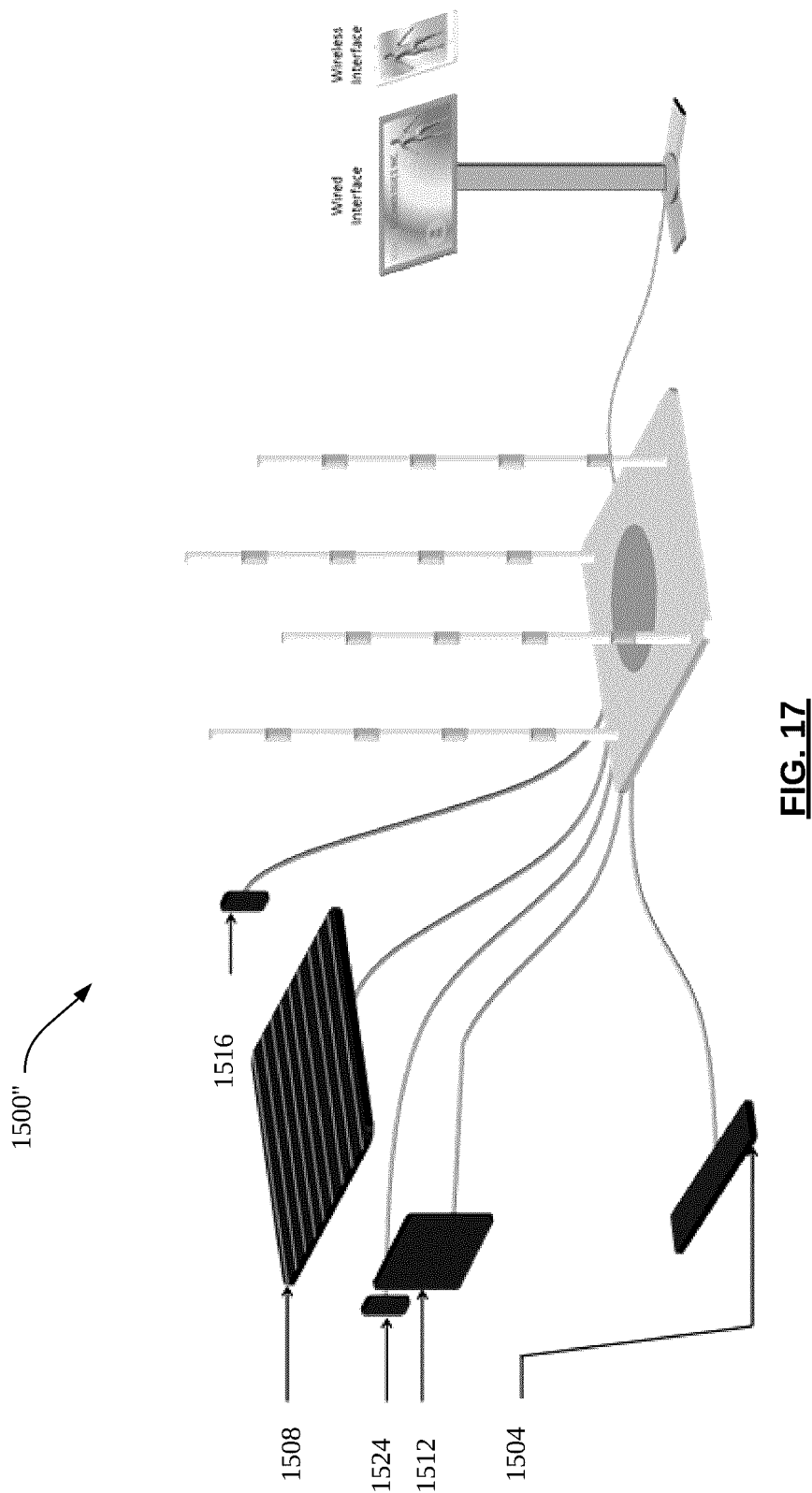
FIG. 17 illustrates a diagrammatic representation of an open concept enhanced 3D body imaging unit according to one embodiment.

FIG. 17 illustrates an open concept enhanced 3D body imaging unit 1500". For example, the sensors 812 and sensing pillars 802 can be located within a pre-existing room. As was the case for the hardware configuration illustrated in FIG. 16, one or more of the components providing the additional functionalities (ex: power storage unit 1504, solar panels 1508, climate control subsystem 1512) may be located externally to the room in which sensors (612, 812, 1312) and sensing pillars (610, 810) are installed.

According to various example embodiments, and as illustrated in FIGS. 15 to 17, the enhanced 3D body imaging unit may further include a wireless communication submodule 1524 that is operable to be in long-range data communication with an electronic device that is located remotely of the plurality of sensors. The wireless communication submodule 1524 can provide wireless communication according to various known data communication protocols and/or standards, such as broadband cellular network technology. The wireless communication submodule 1524 can be useful in situations where the enhanced 3D body imaging unit is deployed at a remote location. For example, despite being deployed at a remote location, the wireless communication submodule 1524 still permits communication with a centralized remote server.

In a remote location where communication with a centralized remote server is not available, processing of the captured 3D data can be performed locally to obtain and generate the full 3D image of the user's body. Thereby, allowing one or more users located at the remote location to view 3D image data immediately.

At the remote location where communication with a centralized remote server is sporadic and unreliable, data can be first stored locally on the system until a connection is established for data transmission, such as using wireless submodule 1524 as described elsewhere herein. The locally stored data and the transmitted data can be encrypted to maintain security and privacy of that data.

Various components described herein with reference to FIGS. 15 to 17 and providing additional functionalities of the enhanced 3D body imaging unit may also be provided as part of the kit for a 3D body imaging unit.

Figure 18:
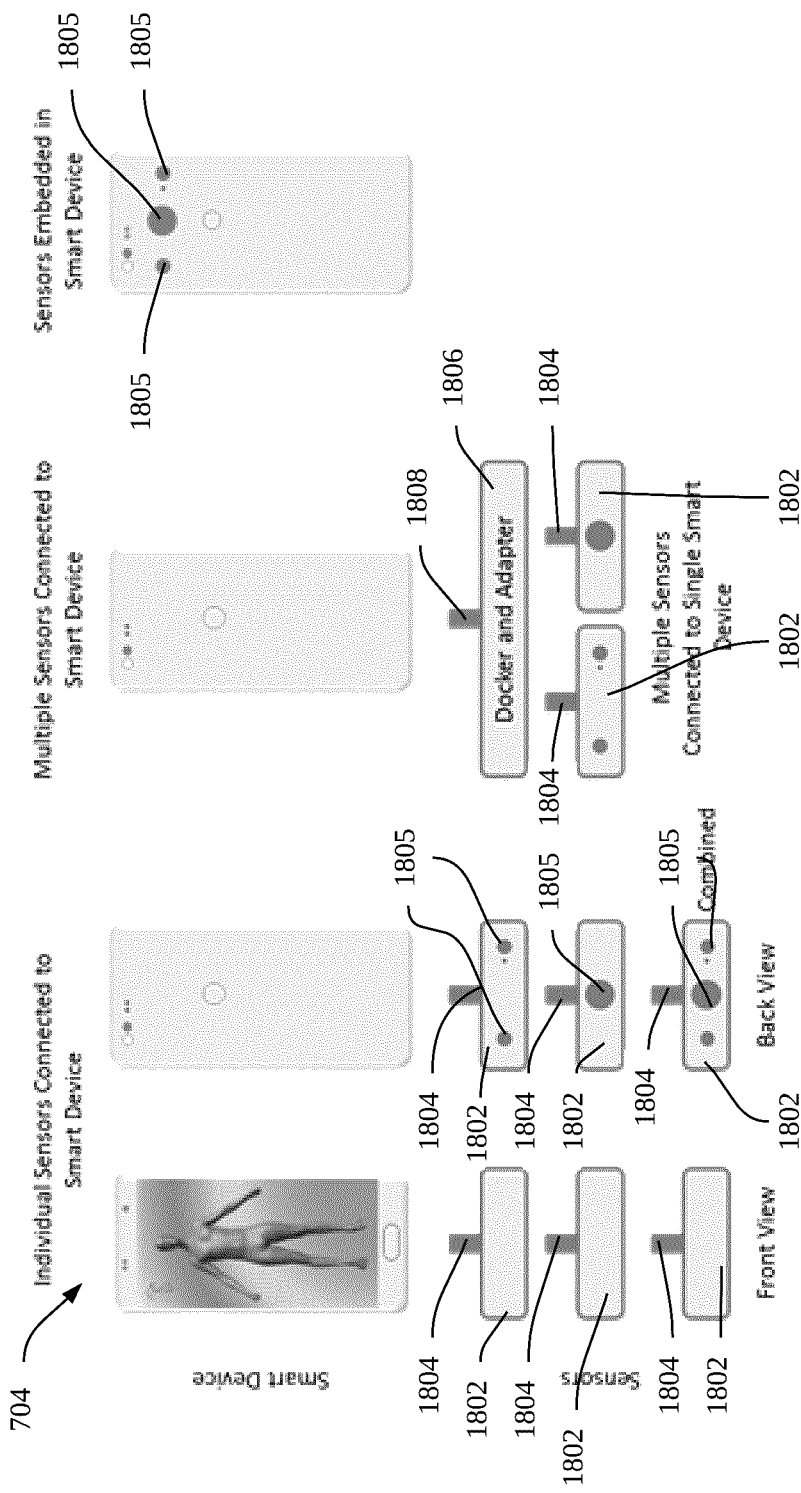
FIG. 18 illustrates a diagrammatic representation of connection adapters according to various embodiments.

FIG. 18 illustrates diagrammatic representation according to various example embodiments of connections of sensors of the 3D body imaging unit to a user device having a processing unit. The user device 704, which may be a smart device such as a smartphone, may be used within this context to control capturing of 3D images by the sensors. The user device 704 can also be operable to process the captured 3D images and to generate the full 3D image of a user's body.

In one example embodiment, each sensor 1802 (also 612, 812, 1312) can include one or more input/output ports 1804 that are connectable to the smart device 704. The adapter may be connected to the smart device using standard ports available within the industry, such as a lightning port or micro-usb. It will be appreciated that the sensors 1802 may be connected in a daisy chain with at least one of the sensors 1802 being further connected to the smart device 704. Lens 1805 of imaging units of each sensor 1802 can be located on a front face of each sensor 1802.

In another example embodiment, a dock 1806 has an input/out 1808 port that is connectable to the smart device 704. The dock 1806 is also connectable to two or more sensors 1802, that each have input/output ports 1804 for connecting to the dock 1806.

In yet another example embodiment, the sensors 1802 may be built-in directly into the smart device 704.

According to an exemplary method for deploying a 3D body imaging unit at a remote location, a kit for a 3D body imaging unit is provided. As described elsewhere herein, the sensing pillars are initially provided in their disassembled configuration. The kit can be transported to the remote location for deployment.

At the deployment site at the remote location, the pillar segments are assembled into their assembled configuration to form one or more sensing pillars (610, 810). Where the sensors are not initially attached to the pillar segments, the sensors can be attached to the formed sensing pillars. As described elsewhere herein, the sensors are oriented so that their fields of view substantially overlap and such that the aggregate of the fields of view cover a space to be occupied by a user's body. A sensing mat can also be placed within the space to indicate where users should position themselves.

As also described herein, the formed sensing pillars may be positioned within an enclosure of the kit or with a pre-existing room of the remote location. Where an enclosure is used, the method includes assembling the enclosure. The sensors (612, 812, 1312) are connected to the system interface, which may be a touchscreen 702, mobile interface 704 or computer interface 706.

Where the kit is for an enhanced 3D body imaging unit, the components providing the additional functionalities are then installed. This may include connecting the power storage unit 104, installing the solar panels 1508, installing the climate control subsystem 1512 and thermostat 1516 and/or installing the wireless communication submodule 524. The fully assembled 3D body image unit is then ready for operation at the remote location.

Although certain embodiments and exemplary hardware configurations were described herein, it is appreciated that a number of other configurations can be provided without departing from the scope of the invention. While specific embodiments have been described and illustrated, it is understood that many changes, modifications, variations and combinations thereof could be made without departing from the scope of the invention.

The invention claimed is:

1. A kit for capturing a 3D image of a body of a user, the kit comprising:
   a plurality of pillar segments being configurable between an assembled configuration and a disassembled configuration,
      in the assembled configuration, the pillar segments being joined to form at least one upstanding sensing pillar having an elongated body defining a vertical axis;
   a plurality of sensors each defining a respective field of view and being configured to be supported on the elongated body of the at least one upstanding sensing pillar when formed and to be distributed along the vertical axis to have overlapping fields of view, the sensors being operable to capture image data of the body of the user;
   an enclosure sized to substantially enclose the at least one upstanding sensing pillar when formed and to receive the user;
   a climate control subsystem operable to control one or more environmental conditions present within the enclosure; and
   a thermostat operable to sense at least one environmental condition within the enclosure and to control the climate control subsystem to adjust the at least one environmental condition present in the enclosure to a predetermined setpoint.

2. The kit of claim 1, wherein the pillar segments are joined to form a plurality of upstanding sensing pillars when in the assembled configuration; and
   wherein at least two of the pillar segments configured to be joined to form one of the upstanding sensing pillars are detached from one another when in the disassembled configuration.

3. The kit of claim 1, further comprising at least one carrying case for enclosing and transporting the sensing pillars in the disassembled configuration.

4. The kit of claim 1, further comprising at least one processing unit connectable to the plurality of sensors to be in data communication therewith and configured to:
   receive the image data captured by the sensors; and
   to process the image data to generate the 3D image of the body of the user.

5. The kit of claim 4, wherein the processing unit is further configured to generate a population model from 3D images of a plurality of different users' bodies.

6. The kit of claim 4, wherein the processing unit is further configured to standardize and normalize a body position of the user in the generated 3D image.

7. The kit of claim 4, wherein the processing unit is further configured to compare 3D images of the body of the user captured during separate imaging sessions.

8. The kit of claim 4, wherein the processing unit is further configured to analyze the 3D image in order to identify physical traits and features indicative of a medical condition of the user.

9. The kit of claim 4, further comprising a wireless communication submodule configured for being in data communication with the processing unit and for transmitting one or more of the captured image data and the generated 3D image of the body of the user to an electronic device located remotely of the plurality of sensors.

10. The kit of claim 1, further comprising a standing mat for supporting the user, the standing mat being placeable in proximity of the at least upstanding sensing pillar when formed and within the overlapping fields of view of the plurality of sensors.

11. The kit of claim 1, further comprising a rechargeable power storage unit for storing electrical energy for powering the plurality of sensors.

12. A system for capturing a 3D image of a user's body, the system comprising:
   a plurality of sensing pillars positioned to surround the user's body and capture image data thereof from different perspectives, each sensing pillar comprising:
      an elongated body extending along a vertical axis, said elongated body being formed from a plurality of assembled segments movable between an assembled configuration in which the segments are secured to one another to form the elongated body, and a disassembled configuration in which the segments are separated from one another; and
      a plurality of sensors supported on the elongated body and distributed along the vertical axis with overlapping fields of view, the sensors being operable to capture image and feature data of the user's body;
   at least one processing unit in communication with the sensing pillars, the processing unit being operable to receive the image data from the sensors and process the image data in order to form the 3D image of the user's body;

an enclosure sized to substantially enclose the plurality of upstanding sensing pillars when formed and to receive the user;

a climate control subsystem operable to control one or more environmental conditions present within the enclosure; and a thermostat operable to sense at least one environmental condition within the enclosure and to control the climate control subsystem to adjust the at least one environmental condition present in the enclosure to a predetermined setpoint.

13. The system according to claim 12, further comprising a carrying case for transporting the sensing pillars in the disassembled configuration.

14. The system according to claim 12, wherein the processing unit is further operable to generate a population model from 3D images of a plurality of different users' bodies.

15. The system according to claim 12, wherein the processing unit is operable to standardize and normalize a body position of the user in the generated 3D image.

16. The system according to claim 12, wherein the processing unit is operable to compare 3D images of a user captured during separate imaging sessions.

17. The system according to claim 12, wherein the processing unit is operable to analyze the 3D image in order to identify physical traits and features indicative of a medical condition of the user.

18. The system according to claim 12, further comprising a wireless communication submodule configured for being in data communication with the processing unit and to transmit one or more of the captured image data and the generated 3D image of the body of the user to an electronic device located remotely of the plurality of sensors.

19. The system according to claim 12, further comprising a standing mat for supporting the user, the standing mat being placeable in proximity of the at least upstanding sensing pillar when formed and within the overlapping fields of view of the plurality of sensors.

20. The system according to claim 12, further comprising a rechargeable power storage unit for storing electrical energy for powering the plurality of sensors.

* * * * *